US010380499B2

(12) United States Patent
Ylipaavalniemi et al.

(10) Patent No.: US 10,380,499 B2
(45) Date of Patent: Aug. 13, 2019

(54) MACHINE-LEARNING SYSTEM FOR OPTIMISING THE PERFORMANCE OF A BIOMETRIC SYSTEM

(71) Applicant: Accenture Global Services Limited, Dublin (IE)

(72) Inventors: Jarkko Ylipaavalniemi, Espoo (FI); Thomas Jean Georges M. Moretti, Nice (FR); Alastair R. Partington, Hatfield (GB)

(73) Assignee: Accenture Global Services Limited, Dublin (IE)

( * ) Notice: Subject to any disclaimer, the term of this patent is extended or adjusted under 35 U.S.C. 154(b) by 756 days.

(21) Appl. No.: 14/836,636

(22) Filed: Aug. 26, 2015

(65) Prior Publication Data

US 2016/0063397 A1    Mar. 3, 2016

(30) Foreign Application Priority Data

Aug. 29, 2014    (EP) .................................... 14290258

(51) Int. Cl.
*G06N 20/00*    (2019.01)
*G06K 9/62*    (2006.01)

(52) U.S. Cl.
CPC ........... *G06N 20/00* (2019.01); *G06K 9/6221* (2013.01); *G06K 9/6262* (2013.01); *G06K 9/6277* (2013.01)

(58) Field of Classification Search
CPC .. G06K 9/6221; G06K 9/6262; G06K 9/6277; G06K 9/00288; G06K 9/00;

(Continued)

(56) References Cited

U.S. PATENT DOCUMENTS

| 2003/0077586 A1* | 4/2003 | Pavlovic ................. G06F 19/18 435/6.14 |
| 2006/0093208 A1* | 5/2006 | Li ....................... G06K 9/00288 382/159 |

(Continued)

FOREIGN PATENT DOCUMENTS

| EP | 2113867 A2 | 11/2009 |
| EP | 2584491 A1 | 4/2013 |
| KR | 2007-0099775 A | 10/2007 |

OTHER PUBLICATIONS

'Ensemble based systems in decision making': Polikar, 2006, IEEE, 1531-636.*

(Continued)

*Primary Examiner* — Robert A Cassity
*Assistant Examiner* — Peter D Coughlan
(74) *Attorney, Agent, or Firm* — Harrity & Harrity, LLP

(57) ABSTRACT

Summarizing, the application relates to a machine-learning system for adaptively changing a matching threshold of a biometric system. The machine-learning system comprises a batch aggregator device operable to receive input data from the biometric system via a communication interface and to aggregate a batch of at least some of the received input data. The machine-learning system further comprises a learning expert device operable to compute a new suggestion for a matching threshold value of the biometric system based on the aggregated batch. Finally, the machine-learning system comprises an output device operable to output the computed new suggestion for the matching threshold of the biometric system via the communication interface.

20 Claims, 14 Drawing Sheets

(58) Field of Classification Search
CPC . G06N 99/005; G06F 17/30867; G06F 21/32; G06F 17/30; H04L 29/06
See application file for complete search history.

(56) References Cited

U.S. PATENT DOCUMENTS

2008/0172725 A1* 7/2008 Fujii ................. G06F 21/32
726/5
2008/0270329 A1* 10/2008 Long ................. G06K 9/6256
706/12
2014/0180994 A1* 6/2014 Llobera ............... G06N 5/02
706/46

OTHER PUBLICATIONS

Extended European Search report corresponding to EP 14 290 258.4, dated Feb. 2, 2015, 11 pages.

* cited by examiner

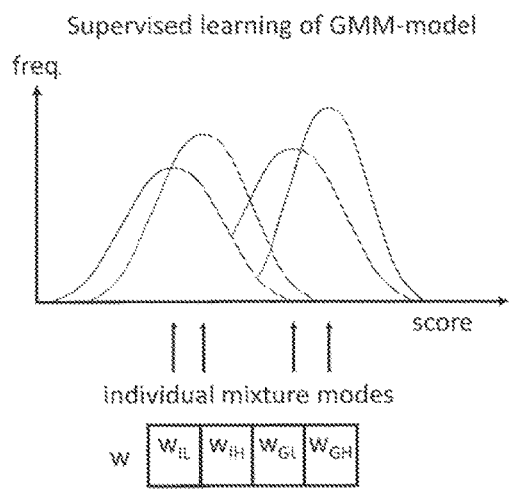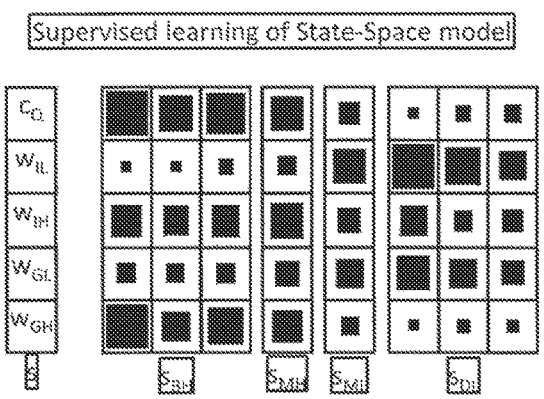
Fig. 13A                                    Fig. 13B

MACHINE-LEARNING SYSTEM FOR OPTIMISING THE PERFORMANCE OF A BIOMETRIC SYSTEM

RELATED APPLICATION

This application claims priority to European Patent Application No. 14290258.4, filed Aug. 29, 2014 the disclosure of which is incorporated by reference herein in its entirety.

TECHNICAL FIELD

The following relates to a machine-learning system for adaptively changing a matching threshold in a biometric system. In particular, the machine-learning system is operable to learn from continuous data received from the biometric system in order to adapt to changes surrounding the biometric system, e.g. to changes in data quality, in environmental conditions and/or in subject demographics, to prevent fraud attempts or single incidents more efficiently.

BACKGROUND

Identity recognition performed by biometric systems is not a binary task. In particular, in determining whether a person is or is not the person he or she claims to be, biometric systems cannot provide an absolute answer. Rather, biometric systems need to utilize a sliding scale where a similarity of two persons' biometric data samples (in the following also referred to as samples) is determined with a certain level of confidence. Such a degree of similarity can be provided by a numerical value that may be called a matching score. The matching score may vary between two boundaries, wherein a first boundary may represent a case where two biometric data samples are not similar and a second boundary may represent a case where the two biometric data samples are identical. In order to make a decision as to whether the two biometric data samples are a match or not, a matching threshold may be determined. The matching threshold may define whether a matching score indicates a match, i.e. the biometric data samples are similar, or a non-match, i.e. the biometric data are not similar.

For example, matching score boundaries may be defined on a scale of [0-100] where 100 may represent a perfect match and 0 may represent a non-match. An exemplary matching threshold may be set at 75. Accordingly, any matching score above this threshold may be considered as a match and any matching score below this threshold may be considered as a non-match. The closer the matching score is to the upper boundary, the more certain a match is.

In addition to the uncertainty in biometric identity recognition as outlined above, changes in the quality of captured biometric data samples, changes in environmental conditions, and/or fraud attempts, can also affect a matching score. Accordingly, a situation where the matching score of two biometric data samples of the same person is below the matching threshold may be defined as a "False Rejection", or "False Non-Match", and the situation where the matching score of two biometric data samples of two distinct persons is above the matching threshold is defined as "False Acceptance" or "False Match".

In practice, it is not possible to predefine a perfect matching threshold for a biometric system. Therefore, for each biometric system, a threshold value is typically defined once by performing a benchmark test/benchmarking on a representative biometric data sample before deployment of the biometric system.

However, during operation of the biometric system, deviations from expected conditions may appear, e.g. in data quality, in environmental conditions, and/or in subject demographics. Accordingly, in conventional biometric systems, a problem arises that in such situations 1) the security of the biometric system can decrease due to false acceptance of non-matching biometric data samples, or 2) the biometric system may become unusable due to false rejection of matching biometric data samples. For example, when using a facial recognition system, e.g. in an Automatic Border Control (ABC) eGate, an automated identification or verification of persons passing a border may be performed. Identification and/or verification may be performed using digital images or video frames of a video source may be performed. Such identification and/or verification may be performed by comparing selected facial biometric identifiers from the image (i.e. a biometric data sample) with facial biometric identifiers (i.e. biometric data samples) stored in a corresponding database. However, environmental conditions, e.g. a lighting intensity or angles, in the area of the ABC eGate may vary throughout a day. Such environmental conditions may become a factor in a False Acceptance Rate (FAR, also called False Match Rate, FMR) or False Rejection Rate (FRR, also called False Non-Match Rate, FNMR) of the facial recognition system. As another example, passenger demographics at the border using the ABC eGate may change e.g. due to planes arriving from different continents. This might also become a factor in the FAR or FRR of the facial recognition system.

In order to address these problems, conventional biometric systems use a static matching threshold value that may be manually fine-tuned by a system administrator during benchmarking or operation of the biometric system. In a further example, the biometric system may be monitored by a monitoring system. If the monitoring system observes unacceptable values for the FAR and/or the FRR, an alarm message for the system administrator of the biometric system may be triggered. Upon receiving the alarm message, the system administrator may manually fine-tune the matching threshold.

Accordingly, there is a need for an improved biometric system that can adapt to changes surrounding the biometric system, e.g. changes in data quality, in environmental conditions and/or in subject demographics in order to prevent fraud attempts or single incidents more efficiently.

GLOSSARY

Machine Learning may relate to constructing systems, i.e. machine-learning systems, having the ability to learn from data.

A Machine Learning System may relate to system that is able to learn from data. In particular, a machine-learning system may be pre-trained on data, e.g. on biometric data samples, using a representative data set. Further to the training, a machine-learning system may be continuously provided with further biometric data samples and may be able to continuously learn during operation of the biometric system by processing the further biometric data samples. Processing further biometric data samples may comprise utilizing one or more of the plurality of machine-learning algorithms known in the relevant art. Accordingly, such a system may adapt to changes in the input data, e.g. changes in the quality of the data and/or in environmental conditions represented by the data. In a next step, the machine-learning system may provide another system, e.g. a biometric system, with recommendations based on the adaptation to changes in the input data, e.g. with a correspondingly adapted matching threshold. Example implementations of a machine-learning system will be provided throughout the description.

Biometrics may relate to human characteristics and traits. In the computing environment, biometrics may be used for identification and access control.

Biometric Identifiers may be distinctive, measurable characteristics that may be used to describe individuals. In particular, biometric data samples may be categorized as physiological characteristics being related to a shape of a human body, e.g. a fingerprint, an iris, a retina, and/or a face. Alternatively, biometric data samples may be categorized as behavioral characteristics being related to a behavioral pattern of a person.

A Biometric Data Sample (Sample) may be a data sample representing a biometric identifier.

A Biometric System may relate to a system operable to process biometric data samples in order to verify an identity of a person providing the respective biometric data sample. Biometric Systems may comprise one or more sources of biometric data samples, e.g., fingerprint readers, facial recognition systems, retinal scanners, and/or iris scanners. Fingerprint readers perform fingerprint recognition or fingerprint authentication by verifying a match between two biometric data samples of human fingerprints (or at least provide data which can be used in this regard). Facial recognition systems operate to automatically identify and/or verify a person (or at least to provide data which can be used in this regard) from a digital image or a video frame of a video source e.g. by generating a biometric data sample from selected facial biometric identifiers of the image with a biometric data sample representing a biometric identifier stored in a database. Retinal scanners operate to identify or verify a person (or at least to provide data which can be used in this regard) from biometric data samples representing unique patterns on a person's retina. Iris scanners operate to automatically identify and/or verify a person (or at least to provide data which can be used in this regard) from a biometric data sample retrieved from a video image of the irises of an individual's eyes.

In the following, a detailed description of examples will be given with reference to the drawings. It should be understood that various modifications to the examples may be made. In particular, elements of one example may be combined and used in other examples to form new examples.

ASPECTS OF THE INVENTION

According to an aspect of the invention, a machine-learning system is provided for adaptively changing a matching threshold in a biometric system. In particular, the machine-learning system comprises:
a batch aggregator device operable to:
receive, via a communication interface, input data from the biometric system; and
aggregate a batch of at least some of the received input data;
a learning expert device operable to:
compute a new suggestion for a matching threshold value of the biometric system based on the aggregated batch; and
an output device operable to output, via the communication interface, the computed new suggestion for the matching threshold of the biometric system.

A matching threshold of a biometric system may define when a determined matching score is considered to be a match or a non-match. In particular, in a biometric system, identity recognition may not be regarded as a binary problem where the biometric system is able determine whether a person is or is not the person he or she claims to be with an absolute certainty. Rather, identity recognition in a biometric system may refer to a sliding scale where the biometric system may define a similarity of a person's biometric data sample with biometric data samples stored in a corresponding database with a certain level of confidence. Such a defined similarity may be called a matching score. Further, a matching threshold may be defined for the biometric system. Using the matching threshold, the biometric system may define whether given matching score is a match or a non-match. For example, when considering matching score boundaries at [0-100], where 100 may represent a perfect match, a matching threshold may be set at 75. Then, any matching score above this matching threshold may be considered as a match and any matching score below the matching threshold may be considered a non-match.

The above described machine-learning system enables providing a biometric system with a matching threshold that is automatically adapted to changing environmental conditions. The matching threshold adaptation is based on calculations related to input data. In particular, the machine-learning system may receive input data from the biometric system. Optionally, the machine-learning system may receive some of the input data from one or more external systems. Upon receiving the input data, the machine-learning system may aggregate a batch on the received input data. Based on the aggregated batch, a new suggestion for a matching threshold value is computed and output. By computing a new threshold value, the technical effect of an improved security of the biometric system is achieved, since the biometric system is prevented from an inadequately high False Acceptance Rate (FAR). Moreover, the technical effect of an improved reliability of the biometric system is achieved since the biometric system is prevented from an inadequately high False Rejection Rate (FRR). Accordingly, the biometric system keeps operating at an optimal level throughout deployment. Further, there is no need to manually adjust the matching threshold. Another advantage is that the biometric system can be easily adapted to any hardware or environment changes during its lifetime. In particular, changes in hardware may lead to changes in a quality of acquired biometrics. This inevitably leads to a shift in observed matching scores of the underlying biometric system. For example, in the case the biometric system is a face recognition system, a hardware change might be a new camera and/or a new target lighting. Such a change might cause the recorded images to have a different resolution and/or color temperature. As another example, if the underlying biometric system is an outdoor fingerprint recognition system, a hardware change might be newly installed covers near/above a corresponding fingerprint sensor, which may result in differences in humidity and/or ambient lighting. Accordingly, hardware changes may affect the matching scores and the performance of the underlying biometric system. Since the machine-learning system provides an automated adaptation of the matching threshold, it is only a matter of a short period of time until enough new data can be aggregated for the machine-learning system to perform any fine-tuning, e.g. of its model and/or parameters in order to accommodate for the changes. Consequently, no manual interaction such as repetitive benchmarking and/or reconfiguration of the biometric system is necessary in order to restore performance of the system when hardware changes are involved. Consequently, less maintenance and/or updates to the biometric system is necessary, and the total cost of ownership associated with the biometric system is reduced.

According to one embodiment of the machine-learning system, the machine-learning system further comprises:
a second learning expert device operable to compute a second new suggestion for the matching threshold value of the biometric system based on the aggregated batch; and
a comparison device operable to compare the new suggestion for the matching threshold value with the second new suggestion for the matching threshold value and for generating a final suggestion for the matching threshold value based on the comparison;
wherein the output device is operable to output, via the communication interface, the final suggestion for the matching threshold value.

According to another embodiment of the machine-learning system, the input data may include one or more of the following:
biometric data quality measures;
environmental measures;
biometric system performance measures including a False Acceptance Rate, FAR, and a False Rejection Rate, FRR;
state indicators comprising a throughput and a time of a day;
a current matching threshold value;
allowed limits and other constraints comprising a minimum matching threshold value and a maximum FAR;
benchmark testing results.

Some of the input data may be provided as instantaneous values, whereas some of the input data may be time averaged.

Biometric data quality measures may relate to the quality of biometric data samples the biometric system is provided with. For example, if the biometric system contains a facial recognition system operable to automatically identify and/or verify a person from a digital image or a video frame of a video source, the quality of biometric data samples may relate to the quality of the digital images or the video frames the biometric system is provided with.

Environmental measures may relate to data received from environmental sensors, e.g. a photo sensor, a light sensor, a temperature sensor and/or any further sensors suitable for providing data related to environmental measures.

Biometric system performance measures may comprise the performance of the biometric system after deployment. In particular, performance measures may include a False Acceptance Rate (FAR) and a False Rejection Rate (FRR). The FAR describes a probability of a false matches performed by a biometric system, i.e. that a person is identified as a being a person he or she is not. The FRR relates to the number of all false non-matches performed by the biometric system, i.e. that a person is not identified as the person he or she actually is. The FAR and FRR are important measures for each biometric system since if the FAR is too high, the security of the system decreases significantly. For example, when the biometric system is used for access control and the FAR of this biometric system is too high, too many persons that do not have access permission might falsely be provided with access. On the other hand, if the FRR is too high, the reliability and usability of the biometric system significantly decreases. For example, when the biometric system is used for access control and the FRR is too high, many persons that do have access permission may not be provided with access.

The state indicators might relate to indicators describing a state of a biometric system.

Throughput may include a measure of a rate of matches performed by the biometric system for a period of time, wherein the period of time may be predefined. For example, if the biometric system comprises a facial recognition system operable to automatically identify and/or verify a person from a digital image or a video frame of a video source. Throughput may include a measure of an overall rate of individuals arriving and leaving the corresponding matching area, which may, for example, be a passenger identification system at an airport.

Generally, each biometric system is benchmarked before and/or during development. Benchmarking allows an administrator/human supervisor getting an indication on a theoretical performance of the biometric system. Alternatively and/or additionally, benchmarking can be performed after a significant upgrade of a biometric system and/or periodically in order to verify the system's overall performance.

Providing benchmark results to the machine-learning system as input has the advantage that the biometric system may be controlled easily. In particular, the biometric system can perform its control decisions on a higher level. There is no need to rely on trial and error to find suitable changes to the threshold value that would lead to a desired performance. Rather, the user may choose the desired performance in terms of a FAR and/or a FRR and/or an Equal Error Rate (EER) and the machine-learning system may be able to use its knowledge of the benchmark performance model. Accordingly, the machine-learning system can provide an optimal suggestion for the threshold value and the threshold value can be updated automatically to changes in order to try reaching the desired performance. Moreover, the biometric system may provide more reliable measures of the performance of the biometric system than labels and/or estimates on the biometric systems that are acquired during operation of the biometric system. In particular, each benchmark biometric data sample is fully labelled, i.e. each biometric data sample is known to originate from a specific person having specific characteristics. Therefore, a labelled biometric data sample, also referred to hereinafter as dataset, is perfect for benchmarking, validation and/or training the biometric system and/or the machine-learning system. Moreover, during operation of a biometric system, it is not possible to get a label for each sample. Therefore, running biometric systems that are not provided with benchmarking results need to perform multiple attempts of matching due to badly acquired biometric sample. For example, if the underlying biometric system comprises a facial recognition system, the system needs to take multiple pictures of a person in order to generate a match using the multiple pictures. If the biometric system generates a final decision based on the multiple pictures, the final decision may be used in order to label the individual samples. Accordingly, the machine-learning system may learn to adapt the threshold value to changes, e.g. in data quality of the data processed by the biometric system, environmental conditions, e.g. changes in lighting conditions and/or changes in subject demographics while preventing the biometric system from fraud attempts.

According to another embodiment of the machine-learning system, the aggregating the batch of the at least some of the received input data comprises:
  collecting statistics on matches performed by the biometric system;
  wherein the collecting statistics may comprise:
    collecting input scores and output values of the matches performed by the biometric system during a batch window; and
    labelling the matches as true/false matches or true/false non-matches, respectively.

In particular, a batch window may be defined in terms of a size of a batch. A size of a batch may be defined in terms of time and/or in terms of a number of attempted matches. The batch window size may be very small, for example, attempted matches over a minute or two, or even a single attempted match. A small batch window size has the technical advantage of a fast adaptation rate of the matching threshold of the corresponding biometric system. Optionally, the batch window size may be big, such as, e.g., attempted matches over the course of an entire day (or longer), or hundreds of attempted matches (or more). A big batch window size has the technical advantage of requiring fewer computations to be performed for data processing; however, the adaptation rate of the matching threshold of the corresponding biometric system may be slower.

According to another embodiment of the machine-learning system, a normalization device is provided. The normalization device is operable to normalize the data in the batch. In particular, the normalizing the data in the batch may comprise computing additional parameters from data within the aggregated batch, wherein the computing of the additional parameters may comprise one or more of the following:
  computing a mean of the aggregated batch;
  computing a variance of the aggregated batch; and
  computing a histogram of the aggregated batch.

The normalization device may perform pre-processing functionality on the input data by normalizing the input data. Normalizing the input data may comprise unifying different values and dynamic ranges that may be specific to some or all of the input data. For example, some of the input data may be provided as binary values, other input data may be provided as integer values and yet other input data may be provided as real values. The normalization device may utilize a separate normalization function for each source the normalization device receives input data from. Additionally and/or alternatively, the normalization device may apply one normalization function to a plurality of input data provided in the same data format. Alternatively and/or additionally, a range of possible values may be inverted, scaled and/or limited. Further, normalization may include turning one type of values, e.g. binary values, into another type of values, e.g. integer values. Further, normalization may include exclusion of invalid data and/or turning raw measurement signals into numerical values that may be fed in a consistent manner into the learning system. Moreover, if some of the input data is missing, e.g. due to malfunctions or bad environmental conditions, the normalization device may apply missing value imputation representing a process of replacing missing data with substituted values. The normalization device may perform the normalization batch by batch.

After the normalization of the data is finished, the normalization device may compute additional parameters from the normalized data. Computing additional parameters may comprise computing a mean, a variance, and/or a histogram of the normalized data.

Each data sample that may comprise the whole biometric measure and values defined, may be appropriately weighted. For example, a weighting based on quality measures on the input data may be provided. The appropriately weighted data samples may be particularly helpful when a quality of the biometric samples varies a lot and/or the number of overall samples is very low, such as access control systems that are only rarely accessed. Under such conditions, weighting improves the learning mode since only the best quality samples may be used for learning.

According to another embodiment of the machine-learning system, the system stores the batch in a storage device and re-samples the batch for continuous learning. In particular, several batches may be collected and stored. These batches may be re-sampled in that the order of the batches is randomized, such that even individual samples are swapped from batch to batch. The re-sampled batches may be used in the learning mode to improve the learning, since machine learning algorithms require lots of data before converging.

According to another embodiment of the machine-learning system and/or the one or more learning expert devices may comprise one or more internal models. The one or more internal models may be updated based on the aggregated batch using a first machine-learning algorithm. Preferably, each expert device may comprise a performance model, a state-space model and/or an optimal threshold model.

The above feature at least has the technical effect that the security and/or reliability of the underlying biometric system is improved, since updating the internal model according to the aggregated enables calculating an improved new threshold value for the biometric system, since an inadequately high FAR or FRR is prevented.

An aspect of the invention relates to a computer-implemented method for adaptively changing a matching threshold in a biometric system using machine-learning, the method comprising:
  receiving, at a batch aggregator device, input data from the biometric system via a communication interface;
  aggregating, at the batch aggregator device, a batch of at least some of the received input data;
  computing, at a learning expert device, a new suggestion for a matching threshold value of the biometric system based on the aggregated batch; and
  outputting, at an output device the computed new suggestion for the matching threshold of the biometric system via the communication interface.

According to another embodiment, the computer-implemented method, further comprises the steps of:
  computing, at a second learning expert device, a second new suggestion for the matching threshold value of the biometric system based on the aggregated batch;
  comparing, at a comparison device, the new suggestion for the matching threshold value with the second new suggestion for the matching threshold value and for generating a final suggestion for the matching threshold of the biometric system based on the comparison; and
  outputting, by the output device, the final suggestion for the matching threshold value of the biometric system via the communication interface.

According to another embodiment of the computer-implemented method, the input data includes one or more of the following:
  biometric data quality measures;
  environmental measures;

biometric system performance measures including a False Acceptance Rate, FAR, and a False Rejection Rate, FRR;

state indicators comprising a throughput and a time of a day;

a current matching threshold value; and allowed limits and other constraints comprising a minimum matching threshold value and a maximum FAR;

benchmark testing results.

According to another embodiment of the computer-implemented method, aggregating the batch of the at least some of the received input data comprises:

collecting statistics on matches performed by the biometric system;

wherein the collecting statistics may comprise:

collecting input scores and output values of the matches performed by the biometric system during a batch window; and labelling the matches as true/false matches or true/false non-matches, respectively.

According to another embodiment, the computer-implemented method further comprises the steps of:

normalizing, by a normalization device, the data in the batch;

wherein normalizing the data in the batch may comprise computing additional parameters from the data within the aggregated batch; and wherein computing the additional parameters from the data within the aggregated batch may comprise one or more of the following:

computing a mean of the aggregated batch;

computing a variance of the aggregated batch; and computing a histogram of the aggregated batch.

According to another embodiment, the computer-implemented method further comprises:

storing the batch in a storage device;

wherein the batch may be re-sampled for continuous learning.

According to another embodiment of the computer-implemented method, the learning expert device comprises an internal model, wherein the model is updated based on the aggregated batch using a first machine-learning algorithm;

wherein the second learning expert device may comprise a second internal model that is updated based on the second aggregated batch using a second machine-learning algorithm different from the first machine-learning algorithm.

An aspect of the invention relates to a computer program product comprising computer-readable instructions, which, when loaded and executed on computer system and/or networked computer system, cause the computer system and/or networked computer system to perform method steps according to the exemplary embodiments described above.

BRIEF DESCRIPTION OF THE FIGURES

Aspects and/or another embodiments are exemplary described in relation to FIGS. 1 to 14, wherein

FIG. 13A depicts an exemplary GMM generated using supervised learning;

FIG. 13B depicts an exemplary state-space model generated using supervised learning;

DETAILED DESCRIPTION OF THE FIGURES

In the following, a detailed description of examples will be given with references to the figures. It should be understood that various modifications to the examples may be made without deviating from the invention. In particular, one or more elements of the examples may be combined and used in other examples to form new examples.

Figure 1:
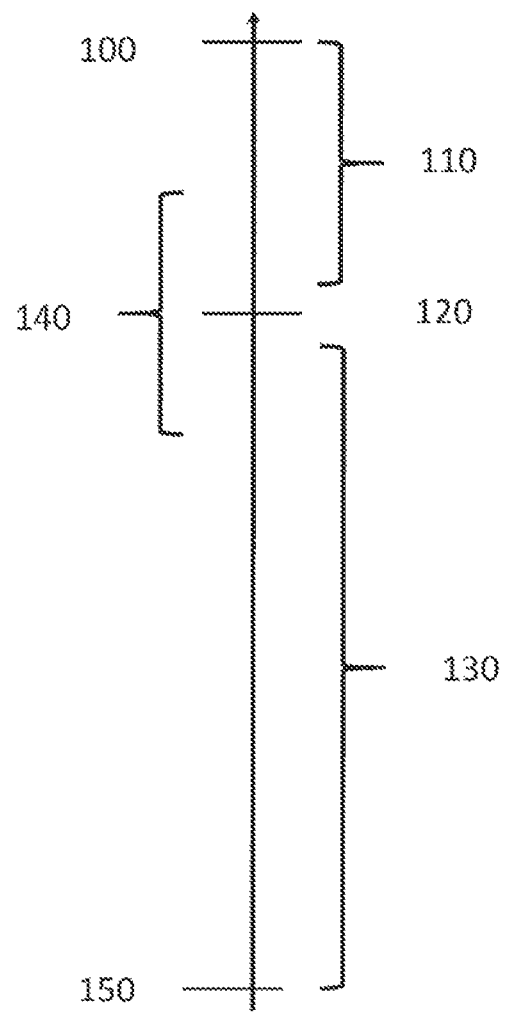
FIG. 1 depicts an exemplary matching threshold of a biometric system.

FIG. 1 illustrates an exemplary representation of a matching threshold 120 of an exemplary biometric system. In particular, since identity recognition performed by the biometric system is not a binary task, biometric systems perform decision-related tasks based on a sliding scale where a similarity of two persons' biometric data samples is determined with a certain level of confidence. Such a degree of similarity can be provided by a numerical value called a matching score. The matching score 360, as described with reference to FIG. 3 below, may vary between two ranges, wherein the first range may represent a case where two biometric data are not similar, i.e. a non-match 130 and the second range may represent a case where the two biometric data are identical, i.e. a match 110. The lower limit 150 for a non-match 130 may be assigned the numerical value "0", wherein the upper limit 100 for a match 110 may be assigned the numerical value "100". The matching threshold 120 may be according to one example assigned the numerical value 75. Accordingly, if a matching score 360—calculated by the biometric system for a specific biometric sample 350—has a numerical value that is equal or greater than the matching threshold 120, the corresponding biometric sample 350 may be considered a match 110. Accordingly, if the matching score 360 is less than the matching threshold 120, the corresponding biometric sample 350 may be considered a non-match 130. Further, a gray zone 140 may be defined. The gray zone 140 may be a numerical range enclosing the matching threshold 120. Accordingly, depending on the security level defined and/or required for the biometric system, biometric samples 350 of persons resulting a matching score 360 within the gray zone may require an additional identity and/or security check of the person that provided the biometric sample 350.

Figure 2:
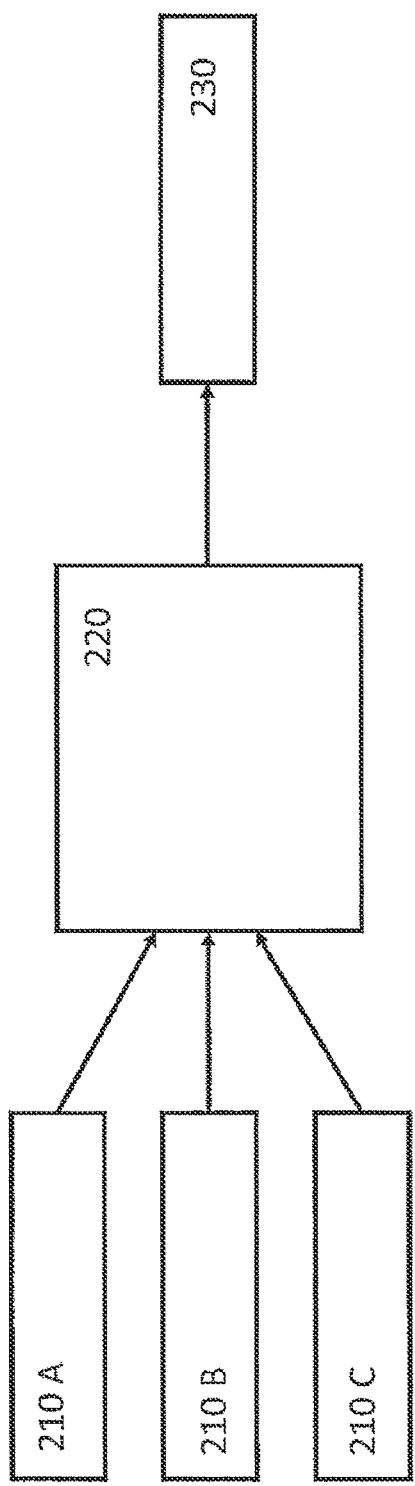
FIG. 2 shows an exemplary machine learning system.

FIG. 2 depicts an exemplary machine learning system 220. In particular, the machine learning system 220 receives, e.g. via a communication interface, input data 210 A to 210 N, (in the following 210 A-N) from a biometric system. The machine learning system 220 may optionally receive some of the input data 210 A-N from external systems. Upon receiving the input data 210 A-N, the machine learning system 220 may aggregate a batch of at least some of the received input data 210 A-N. Based on the aggregated batch, the machine learning system 220 may compute a new suggestion 230 for a matching threshold value of a biometric system, wherein at least a part of the input data 210 A-N may be received from the biometric system. Finally, the machine learning system 220 may output the new suggestion 230 for the new matching threshold value, e.g. via the communication interface. Alternatively and/or additionally to outputting the new suggestion 230 for the matching threshold 120, the machine learning system 220 may output an indication as to whether the current matching threshold 120 should be adapted and/or an indication if the matching threshold 120 should be increased or decreased.

The input data 210 A-N the machine learning system 220 receives from the biometric system and optionally from one or more external systems may include one or more of: biometric data quality measures, environmental measures, biometric system performance measures including a False Acceptance Rate (FAR) and/or a False Rejection Rate (FRR). The FAR describes a probability that a biometric system performs a false match, i.e. that a person is identified as a being a person he or she is not. The FRR describes a probability that a biometric system performs a false non-match, i.e. that a person is not identified as the person he or she actually is. The FAR and FRR are important measures for each biometric system. In particular, if the FAR is too high, the security of the system decreases significantly. For example, when the biometric system is used for access control and the FAR of this biometric system is too high, persons that do not have access permission might falsely be provided with access permission. On the other hand, if the FRR is too high, the reliability and usability of the biometric system significantly decreases. For example, when the biometric system is used for access control and the FRR is too high, persons that do have access permission might falsely not be provided with access permission. The FAR and the FRR will be further described with reference to FIGS. 5A to 7B below. The input data 210 A-N may further comprise state indicators comprising a throughput and a time of a day, a current matching threshold value, allowed limits and other constraints comprising a minimum matching threshold value and a maximum FAR and/or benchmark testing results. The throughput can be a numerical value. Specifically, the throughput can be the number of people passing through the gate. Further, the biometric system may provide some of the input data 210 A-N as instantaneous values, whereas some of the input data 210 A-N may be time averaged.

Biometric data quality measures may relate to a quality of biometric data, e.g. biometric samples 350, the biometric system is provided with. For example, if biometric system comprises a facial recognition system operable to automatically identify and/or verify a person from a digital image or a video frame of a video source, the quality of biometric data may relate to the quality of the digital images or the video frames the biometric system is provided with.

Environmental measures may relate to data received from environmental sensors, e.g. a photo sensor, a light sensor, a temperature sensor and/or any sensor suitable for recording and/or collecting data related to environmental measures. The environmental sensors may be part of the biometric system. Alternatively or additionally, at least some of the environmental sensors may be part of the machine-learning system. Optionally, the environmental sensors may be separate systems.

The above described machine-learning system provides a biometric system with a matching threshold 120 that is adapted based on computations performed on the input data 210 A-N. Hence, the technical effect of an improved performance of the biometric system due to the continuous optimization of the matching threshold is achieved. Therefore, the performance and security of the underlying biometric system is significantly improved. In particular, the continuous optimization of the biometric system leads towards improved security since adaptively adjusting the threshold to different conditions based on input data prevents false determination of a match 110 and/or false determination of a non-match 130.

Figure 3:
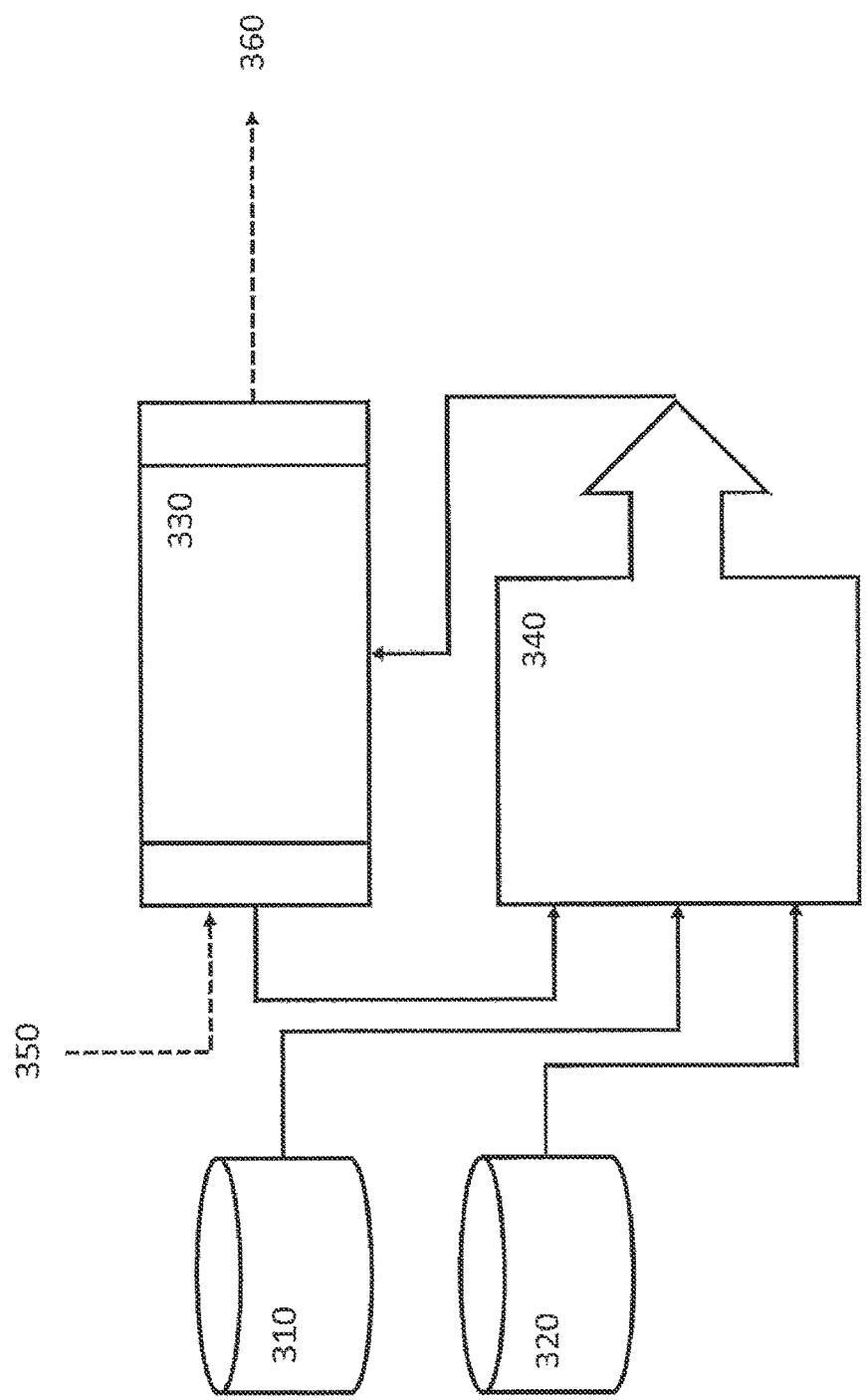
FIG. 3 shows an exemplary interaction of the machine learning system of FIG. 2 with a biometric system.

FIG. 3 depicts an exemplary machine-learning system 340 as described with reference to FIG. 2 above. In particular, the exemplary machine-learning system 340 receives input data from the biometric system 330 as described with reference to FIG. 1 above. The exemplary machine-learning system 340 may receive environmental data 310 from an external system, as well as further input data 320 from a further external system. However, it is to be noted that the machine-learning system 340 may instead receive input data 210 A-N only from the biometric system 330 and/or from further, different systems. In particular, the input data 210 A-N as described with reference to FIG. 2 above may comprise the environmental data 310 and/or the other data 320. Environmental data 310 may comprise data related to environmental conditions surrounding the underlying biometric system, e.g. lighting conditions, humidity, data related to user demographics of users using the biometric system, and the like. Other data 320 may comprise biometric data quality measures, environmental measures, biometric system performance measures including a FAR, a FRR, state indicators comprising a throughput and a time of a day, a current matching threshold value, allowed limits and other constraints comprising a minimum matching threshold value and a maximum FAR and/or benchmark testing results.

Upon receiving the input data 210 A-N, i.e. the environmental data 310 and/or the other data 320, the machine learning system 220 may aggregate a batch of at least some of the received input data 210 A-N. Based on the aggregated batch, the machine learning system 220 computes a new suggestion 230 for a matching threshold value of the biometric system 330. Further details on computing a new suggestion 230 for the matching threshold value of the biometric system 330 will be provided in more detail with reference to FIGS. 8 to 13B below. Finally, the machine learning system 220 may output the new suggestion 230 for a matching threshold 120 to the biometric system 330. Alternatively and/or additionally to outputting the new suggestion 230 for the matching threshold, an indication as to whether the current matching threshold should be adapted and/or an indication if the matching threshold should increase or decrease may be output.

Further, as may be seen in FIG. 3, the biometric system 330 may still perform identity recognition by receiving biometric data/biometric samples 350 and calculating a matching score 360 based on the received biometric data. For example, if the biometric system 330 is a facial recognition system, the biometric system 330 may automatically identify or verify a person from a digital image or a video frame of a video source and output a correspondingly calculated matching score 360, since the biometric system 330 and the machine learning system 340 may operate independently of one another.

Figure 4:
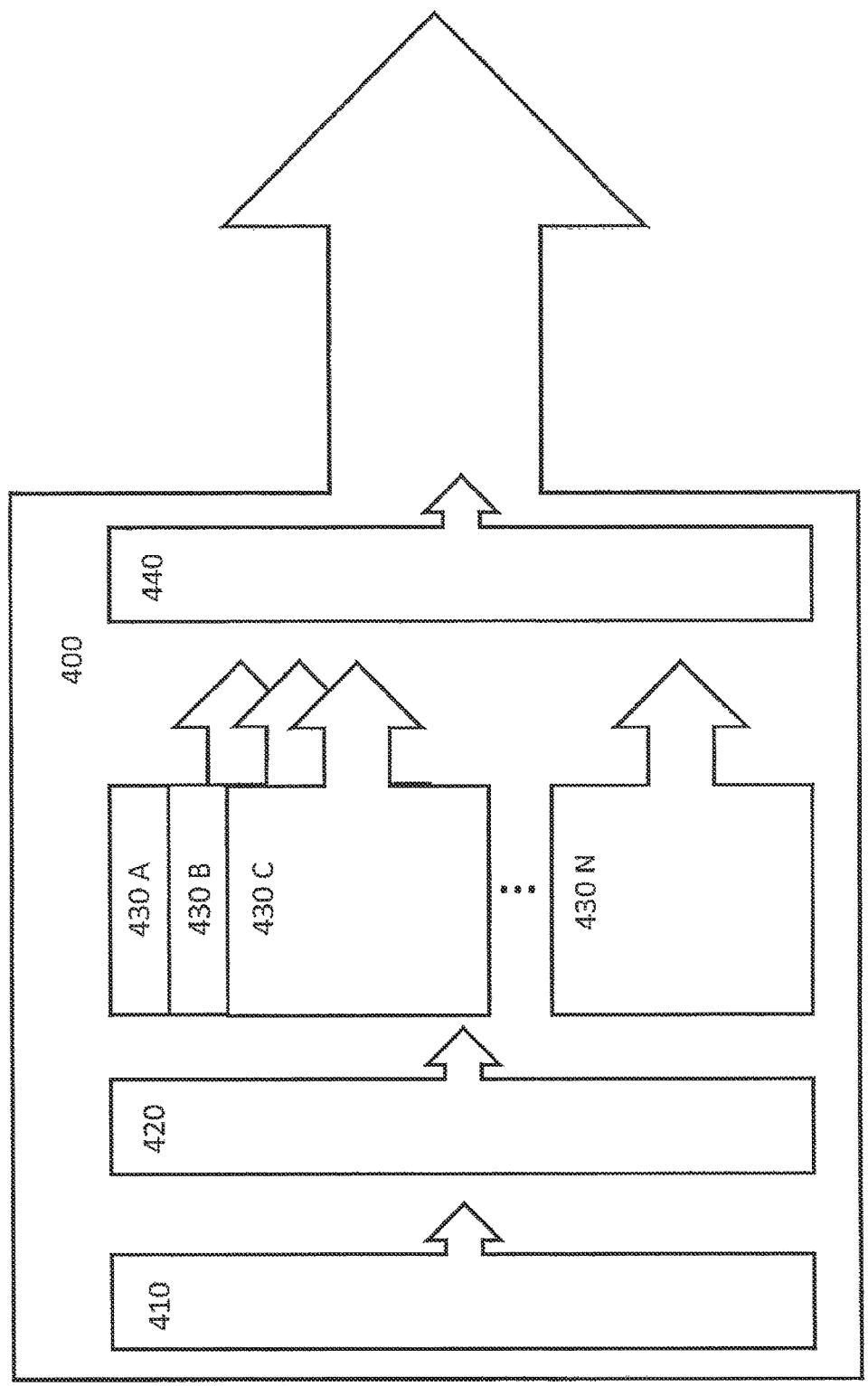
FIG. 4 depicts exemplary components of the machine learning system of FIG. 2.

FIG. 4 depicts another example of a machine-learning system 400 as described with reference to FIGS. 2 and 3 above. In particular, the machine-learning system 400 comprises a batch aggregator device 410 that may be operable to receive input data 210 A-N from the biometric system 330 and/or one or more external systems. For example batch aggregator device 410 may receive the input data 210 A-N via a communication interface. The input data 210 A-N may be input data 210 A-N as described with reference to FIG. 2 above and may comprise the environmental data 310 and/or the other data 320, as described with reference to FIG. 3 above. Upon receiving the input data 210 A-N, i.e. the environmental data 310 and/or the other data 320, the machine learning system 400 may aggregate a batch of at least some of the received input data 210 A-N.

Aggregating the batch of the at least some of the received input data 210 A-N may comprise collecting statistics on matches and/or non-matches performed by the biometric system 330. Collecting statistics may comprise collecting input scores, which may also be referred to as input data, the matches performed by the biometric system 330 during a batch window, which may be pre-defined, and labelling the matches as true matches (TM) and/or false matches (FM) and/or true non-matches (TNM) and/or false non-matches (FNM), respectively.

A batch window may be defined in terms of a size of a corresponding batch. A size of a batch may be defined in terms of time and/or in terms of a number of matches performed by the biometric system. The batch window size may be very small. A small batch window size has the technical advantage of a fast adaptation rate of the matching threshold of the corresponding biometric system 330. Optionally, the batch window size may be big. A big batch window size has the technical advantage of requiring fewer computations to be performed for data processing; however, while the adaptation rate of the matching threshold of the corresponding biometric system 330 may be slower.

Optionally, the machine-learning system 400 may comprise a normalization device 420. The normalization device 420 may normalize the data in the aggregated batch. Normalizing the data in the batch may comprise computing additional parameters from the data within the aggregated batch. Computing the additional parameters may comprise one or more of: computing a mean of the aggregated batch, computing a variance of the aggregated batch, and/or computing a histogram of the aggregated batch.

Accordingly, the normalization device 420 may normalize the input data 210 A-N data in the aggregated batch by performing some pre-processing on said data. Normalizing the input data 210 A-N may comprise unifying different values and/or dynamic ranges that may be provided with the input data 210 A-N. In particular, some of the input data 210 A-N may be provided as binary values, other input data 210 A-N may be provided as integer values and yet other input data 210 A-N may be provided as real values. The normalization device 420 may utilize a separate normalization function. Additionally and/or alternatively, the normalization device 420 may apply a same normalization function to each of a plurality of input data 210 A-N provided in the same data format. Moreover, if some of the input data 210 A-N is missing, e.g. due to malfunctions and/or bad environmental conditions, the normalization device 420 may apply missing value imputation representing a process of replacing missing data with substituted values.

After the normalization of the data in the batch is finished, the normalization device 420 may compute additional parameters from the normalized data. Computing additional parameters may comprise computing a mean, a variance, and/or a histogram of the normalized data. Further, the additional parameters may be appropriately weighted. For example, a weighting may be based on quality measures on the input data 210 A-N.

In addition, the machine-learning system 400 may comprise at least one learning expert device 430 A-N operable to compute a new suggestion 230 for a matching threshold value of the biometric system 330 based on the aggregated batch. An example computation of the new suggestion 230 for the matching threshold value of the biometric system 330 will be provided in more detail with respect to FIGS. 8 to 13B below.

The machine-learning system 400 may further comprise at least a second learning expert device 430 A-N. In this case, the second learning expert device 430 A-N may compute a second new suggestion 230 for the matching threshold value of the biometric system 330 based on the aggregated batch. The second new suggestion 230 for the matching threshold value may be different from the new suggestion 230 for the matching threshold value as received from the first learning expert device 430 A-N. This may be for example realized in that the first learning expert device 430 A-N uses one or more machine-learning algorithms different from one or more machine-learning algorithms used by the second learning expert device 430 A-N. A specific example for the calculating of a new suggestion 230 for a matching threshold value of a biometric system 330 will be provided with respect to FIGS. 8 to 13B below. In this case, the machine-learning system 400 might further comprise a comparison device 440 operable to compare the new suggestion 230 for the matching threshold value with the second new suggestion for the matching threshold value. Based on the comparison, the comparison device 440 might generate a final suggestion for the matching threshold value. Then, the output device may output the final suggestion for the matching threshold value to the biometric system 330. Alternatively and/or additionally to outputting the final suggestion for the matching threshold, an indication as to whether the current matching threshold should be adapted and/or an indication if the matching threshold should increase or decrease may be output. It is noted that the machine learning system 400 is not limited to comprising at most two learning expert devices 430 A-N. Rather, each machine learning system may comprise an arbitrary amount of learning expert devices 430 A-N.

Providing the final suggestion for the matching threshold value using at least two learning expert devices 430 A-N leads to the technical effect of improved security, since the suggestion of the matching threshold is based on at least two comparison devices making at least two different suggestions. Each of the learning expert devices 430 A-N may further comprise one or more internal models (as will be outlined in more detail with respect to FIG. 8 below). The internal models (not shown) of the first and the second learning expert device may comprise one or more different machine-learning algorithms for computing a new suggestion for the matching threshold value 230 of the biometric system based on the aggregated batch. Further details on computing a new suggestion for the matching threshold value of the biometric system will be provided in more detail with reference to FIGS. 8 to 13B below. Since the final suggestion for the new matching threshold value is based on a comparison of the distinct new threshold values based on different internal models, a more accurate matching threshold value is computed, such that the FAR and/or FRR of the biometric system 330 is further reduced.

Benchmarking a Biometric System

Benchmarking of a biometric system 330 may comprise using a large, representative set of biometric data samples corresponding to the biometric system 330, wherein the ground truth of the biometric data samples may be known. Knowing the ground truth of the biometric samples means that for each matching score 360 that is determined by the biometric system 330, the matching score can be correctly labelled as correct or false match and/or as correct or false non-match, i.e. whether the biometric system 330 made the correct decision in calculating a matching score for each biometric data sample. Benchmarking a biometric system 330 may provide an estimation of the overall performance of the biometric system 330 using the ground truth. For example, if the underlying biometric system comprises a face recognition system, a representative set of biometric data samples may comprise all required demographics of persons using the biometric system 330, e.g. gender, age, race, both genuine and impostor biometric samples, and both good quality and bad quality biometric samples. Further, the representative set of biometric samples should comprise biometric samples acquired under different environmental conditions.

Benchmarking may comprise forcing the biometric system 330 to calculate a matching score 360 for each biometric data sample comprised in the representative set of biometric data samples. Further, a score distribution for different sample categories may be calculated. Calculating the score distribution may include calculating frequencies of different matching scores for each sample class and/or sample condition, reporting only the overall genuine vs. the impostor distributions, and/or using all data categories comprised in the representative set of biometric data samples if the data is used in pre-training A sample class may be a class of individuals for a given age, gender, etc. A condition may be relating to an environment, such as lighting, etc. Exemplary data categories may be:
  demographic data of each person in the representative set of biometric data samples, comprising age, gender, race, nationality, disabilities and/or any further factors suitable for affecting capture of a specific biometric sample; and/or
  details of an environment during sample collection for each of the biometric data sample in the representative set of biometric data samples, e.g. brightness, humidity, and/or cooperation of the individual.

Finally, the calculation of the matching scores 360 of each biometric data sample comprised in the representative set of biometric data samples may be repeated using different threshold values. In a next step, the outcome of the different threshold values may be calculated by the machine learning system 220, 330 based on the genuine and impostor score distributions. This allows choosing a suitable threshold value for the biometric system 330 based on its performance needs.

With reference to FIGS. 5A, 5B, 6A, 6B, 7A and 7B some exemplary results of a benchmarking applied to a biometric system are explained. In particular, it will be shown that choosing a good/optimum threshold value significantly depends on the requirements of the biometric system.

Figure 5A:
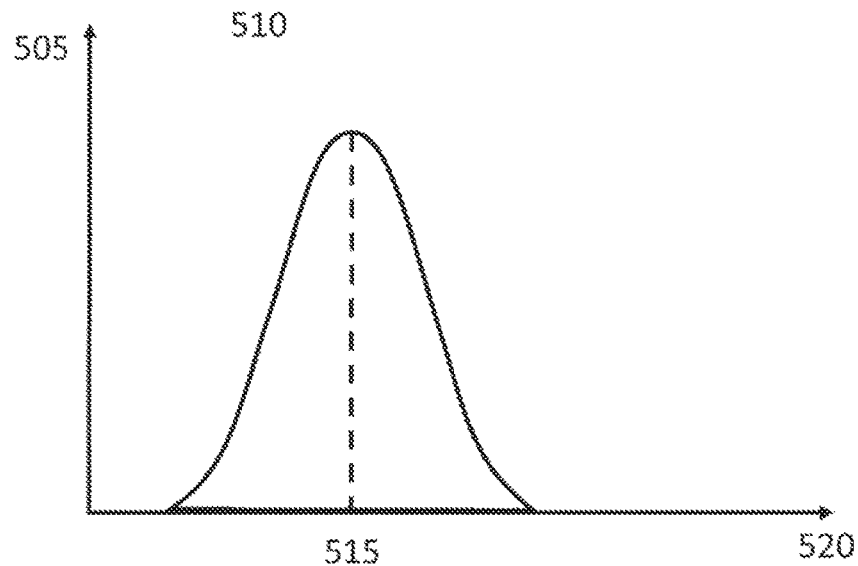
FIG. 5A shows an exemplary impostor score distribution for a sample class.

In particular, FIG. 5A depicts an exemplary impostor score distribution 510 resulting from the benchmarking as performed on the biometric system. In particular, the y-axis may represent a frequency 505 whereas the x-axis may represent a score 520. The peak of the impostor score distribution 510 may represent a mean 515 of the impostor score distribution 510. A high impostor score value may lead towards a high FAR, see FIG. 5B.

Figure 5B:
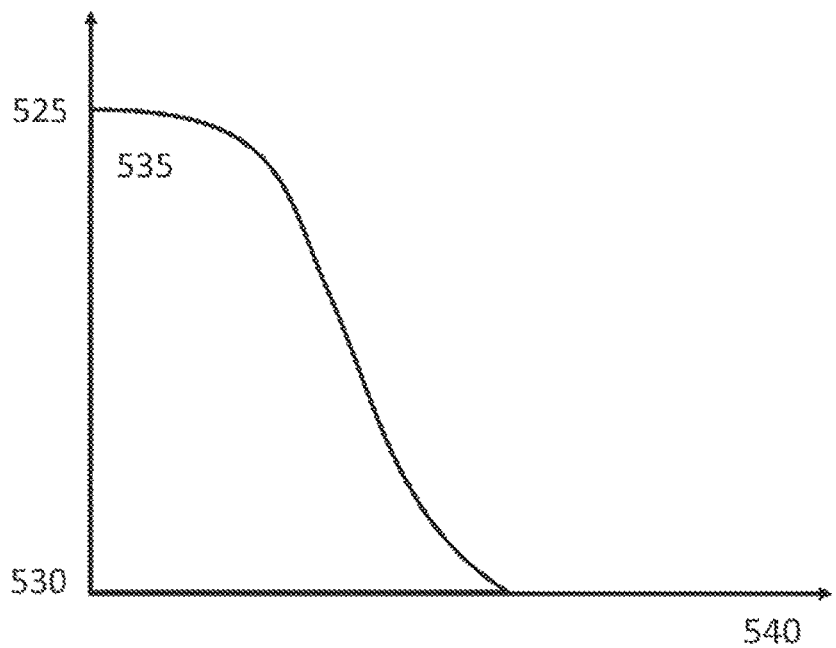
FIG. 5B depicts an exemplary corresponding False Acceptance Rate (FAR) as a function of the threshold value.

FIG. 5B depicts an exemplary corresponding FAR 535 as a function of an underlying threshold value 540. The FAR changes depending on which threshold value is chosen for the biometric system. The FAR may be assigned a value between "0" 530 and "1" 525.

Figure 6A:
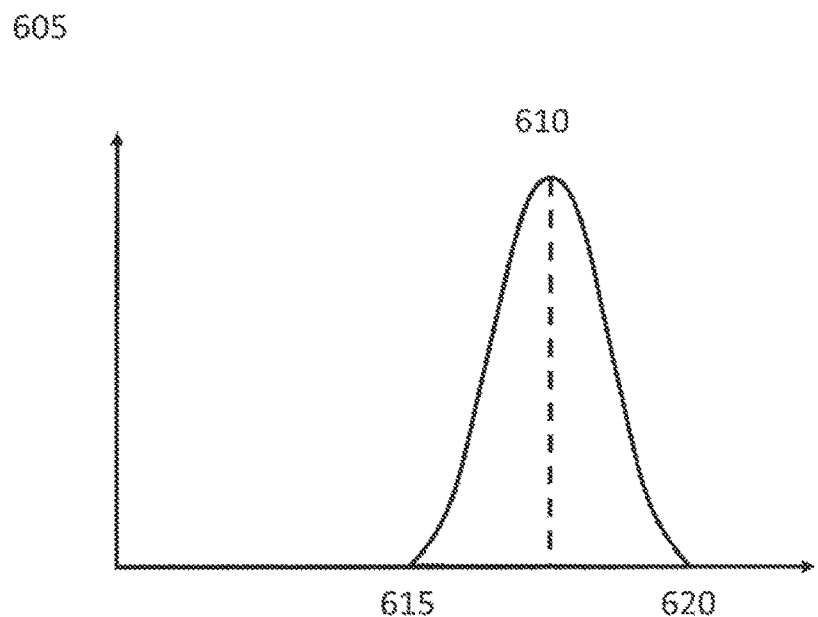
FIG. 6A depicts an exemplary genuine distribution for a sample class.

FIG. 6A depicts an exemplary genuine distribution 610 for a sample class resulting from the benchmarking as performed on the biometric system. In particular, the y-axis may represent a frequency 605 whereas the x-axis may represent a score 620. The peak of the genuine score distribution 610 may represent a mean 615 of the genuine score distribution 510. A high genuine score value may lead towards a high FRR, see FIG. 6B.

Figure 6B:
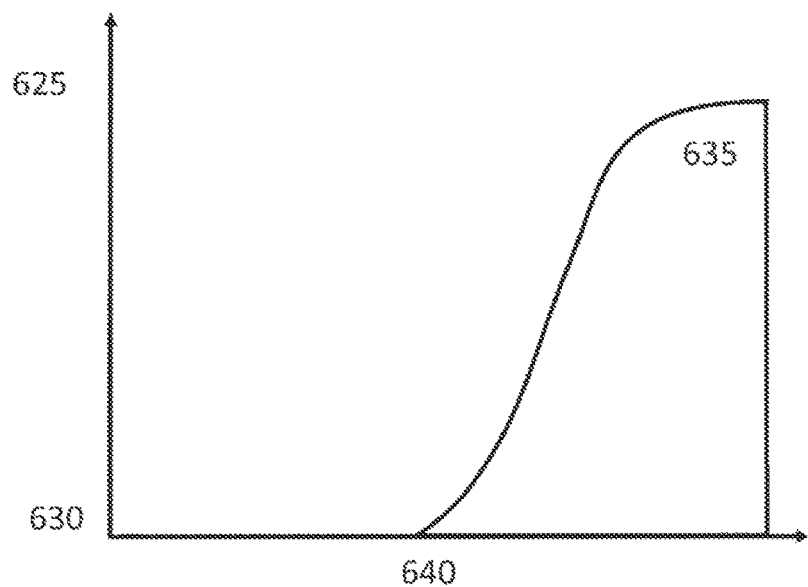
FIG. 6B depicts an exemplary False Rejection Rate (FRR) as a function of the threshold value.

FIG. 6B depicts an exemplary corresponding FRR 635 as a function of an underlying threshold value 640. The FRR may change depending on which threshold value is chosen for the biometric system. The FRR may be assigned a value between "0" 630 and 1 625.

Accordingly, choosing the appropriate threshold value may significantly depend on the requirements of the biometric system. An appropriate threshold value 120 for an underlying biometric system 330 may comprise choosing the threshold value 120 leading to the Equal Error Rate (EER), which will be further explained with reference to FIGS. 7A and 7B below.

Figure 7A:
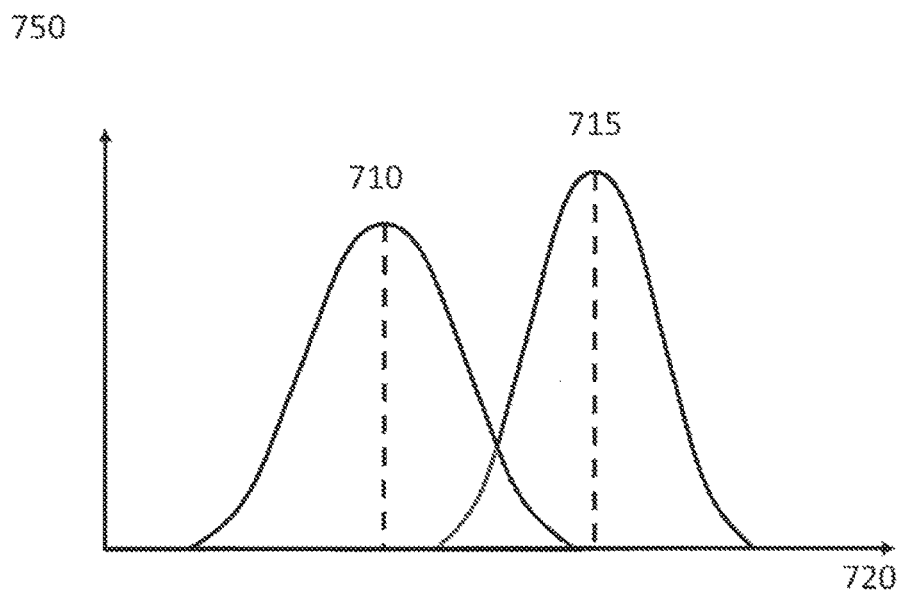
FIG. 7A depicts the exemplary impostor and genuine distributions of FIG. 5A and FIG. 6A, respectively.
Figure 7B:
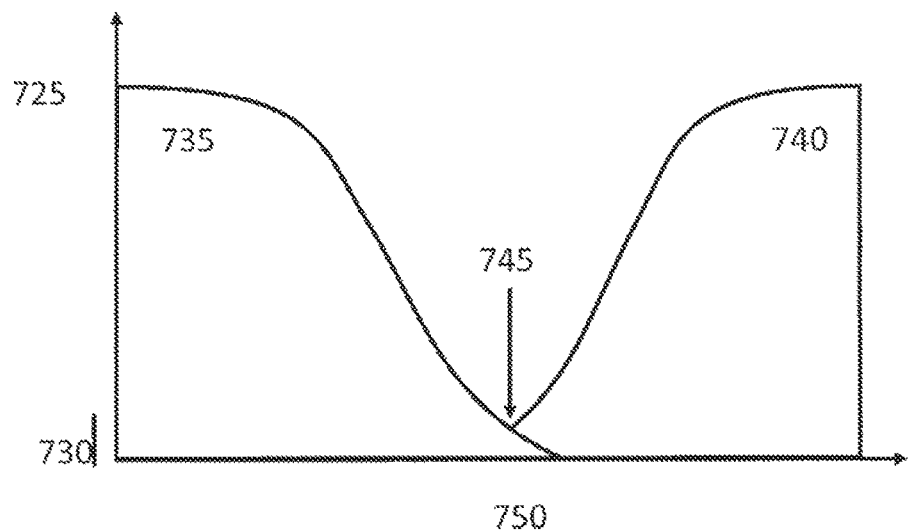
FIG. 7B depicts the exemplary FAR and FRR as depicted in FIG. 5B and FIG. 6B, respectively and an EER of the FAR and the FRR.

FIG. 7A depicts the exemplary impostor 710 and genuine 715 distributions as outlined in FIG. 5A and FIG. 6A, whereas FIG. 7B depicts the exemplary FAR 735 and FRR 740 as depicted in FIG. 5B and FIG. 6B. Moreover, FIG. 7B depicts the EER 745 of the FAR and the FRR, which is located at the intersection 750 of the FAR and the FRR. The FRR/FAR may be assigned a value between "0" 730 and "1" 725; therefore, the EER may also be assigned a value between "0" and "1".

Further, a convenient system may choose a threshold value leading to a higher FAR, wherein a secure system may choose a threshold value leading to a higher FRR.

High Level Design of a Machine-Learning System

Figure 8:
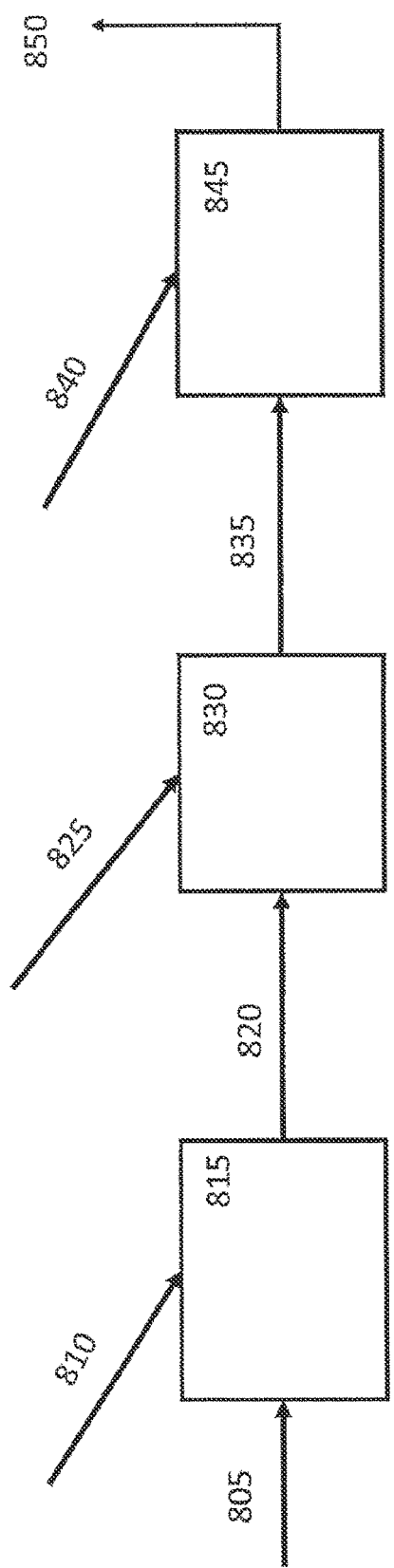
FIG. 8 depicts three separate exemplary steps of a machine-learning system comprising performance modelling, state-space clustering and a threshold selection.

FIG. 8 depicts three separate steps that represent processing steps which may compose a machine-learning system 220, 340, 400, as described with reference to FIGS. 2 to 4 above.

In particular, in a first step, the machine-learning system 220, 340, 400 may generate a performance model of the underlying biometric system 330. The performance model may be generated using matching scores 805 and performance inputs 810 at least partly received from the underlying biometric system. The performance model 815 generated from the matching scores 805 and performance inputs 810 may generate performance model weights 820 as output. In other words, in this first step, a unified performance model of the biometric system is generated regardless of any setup of the biometric system 330. The setup of the biometric system 330 may include implementation requirements and conditions in the biometric system 330 relating to legal, regulatory, security policy, and/or other possible requirements imposed on the design and deployment of the biometric system 330. For example, implementation requirements may result in a limitation of possible input data that may be available for data measurement and/or data collection. As another example, regulations for a particular biometric system 330 may require that the biometric data samples may not be stored in the system, such that no previous batches are available. Therefore, the performance model is trained and fine-tuned under generic conditions. This significantly improves the flexibility of the machine-learning system 220, 340, since it is suitable for biometric systems 330 having different implementation requirements. The performance model 815 may provide best estimates of a True Acceptance Rate (TAR) and/or True Rejection Rate (TRR) and/or FAR and/or FRR. The TAR indicates how frequently a biometric sample 350 of genuine person is accepted correctly by the system, wherein the TRR indicates how frequently a biometric sample 350 of an impostor would be correctly rejected.

Best estimates may be optimal estimates in that if it is known that the underlying performance model 815 fits the biometric data samples 350 as accurately as possible, a high confidence is provided that the calculated TAR, TRR and/or any other performance indicators that are not directly measurable under operating conditions are as accurate as possible. In other words, if the performance model 815 would not provide best estimates, the estimated performance indicators might not be able to be trusted. The performance model 815, also referred hereinafter as a unified performance model 815, may be generated using an algorithm from the Mixture Model Family. More details with respect to generating the performance model 815 of a biometric system 330 will be provided with respect to FIG. 9 below.

In a next step, based on the input of the performance model weights 820 and on some further condition inputs 825, a state-space clustering and classification model 830, in the following also referred to as state-space model, may be generated. In particular, a state-space model may be generated that may describe a current state 835 and changes of the state of the underlying biometric system 330. This model allows an administrator/human supervisor to understand a matching confidence and a stability of the biometric system 330. The model be may generated using an algorithm from the clustering and the classification family. More details with respect to the state-space model will be provided with respect to FIG. 10 below.

Finally, a third step may be the threshold selection 845 that takes as input the current state 835 of a biometric system 330 received from the state-space model 830 and further performance inputs 840. The threshold selection 845 provides a new threshold value 850 based on the inputs. In particular, an optimal threshold model may be generated that may match a required performance to an actual performance model in a current state 835. The matching of the required performance to the actual performance model provides the technical advantage of an automatic choice of the optimal threshold 850 leading to the desired performance of the biometric system 330. To do so, an algorithm that may be a simple inference from the model may be used. More details with respect to the optimal threshold model will be provided with respect to FIGS. 9 and 13B below.

Figure 9:
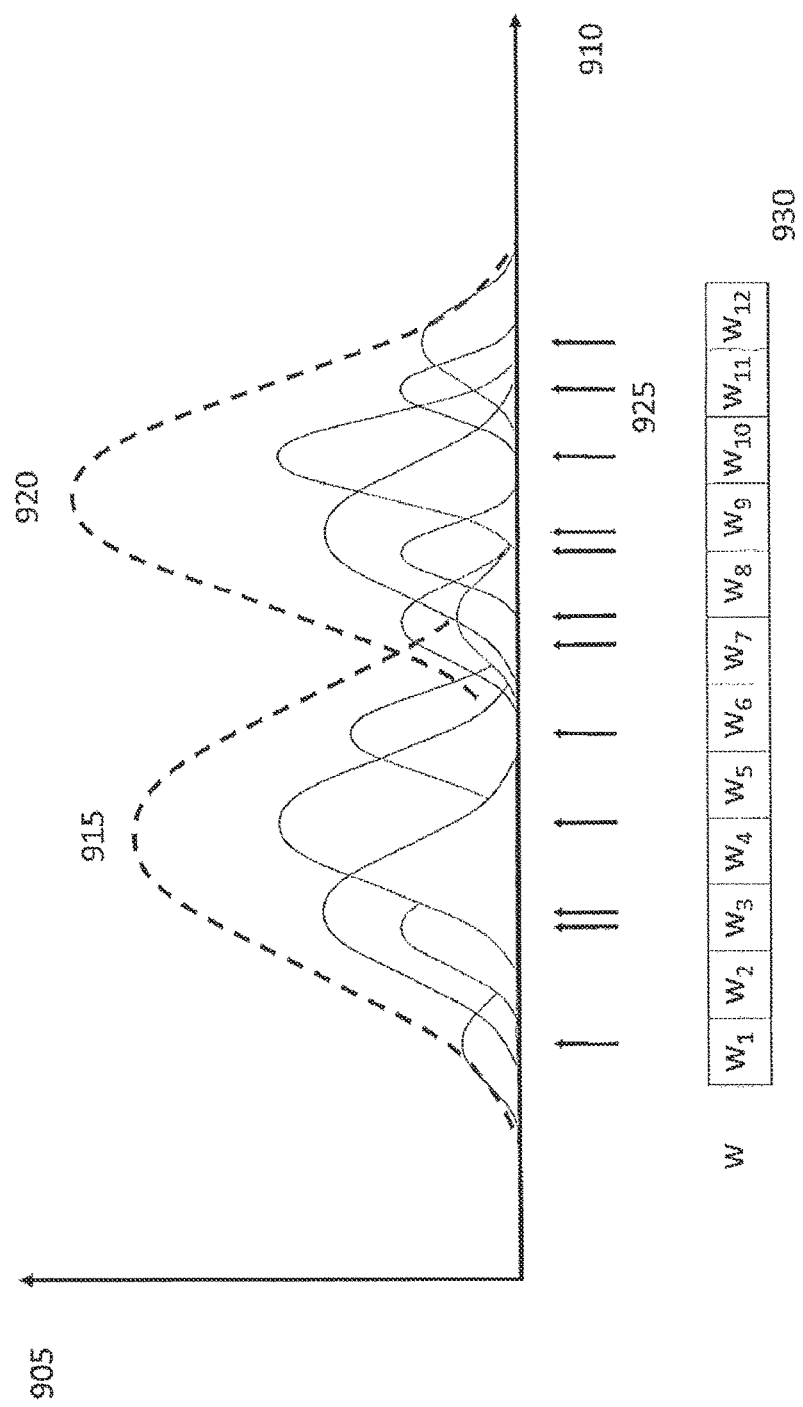
FIG. 9 shows an exemplary GMM representing a performance model of a biometric system.

FIG. 9 shows how an exemplary performance model 815 of an exemplary biometric system 330, as introduced with reference to FIG. 8 above, may be generated. In particular, as performance model 815, a Gaussian Mixture Model (GMM) may be generated, given the input of matching scores 805 that may comprise normally distributed estimation errors with biometric samples and a measurement of noise of a biometric system 330.

One or more training algorithms may be selected from the plurality of training algorithms known in the art, i.e. unsupervised or supervised training algorithms. Supervised training algorithms related to the GMM may be e.g. a statistical method of an expectation maximization (EM) algorithm that requires a given constant value for a number of mixture modes (K) and some form of expert initialization that is not too far from an expected optimum. Unsupervised training algorithms may comprise clustering or model selection which enable a machine learning system to also learn an optimal value of K without the requirement of a special initialization. In particular, one or more supervised and one or more unsupervised training algorithms may be selected for benchmarking and a pre-training of the biometric system 330, i.e. before deployment of the biometric system 330. One or more supervised training algorithms may be further chosen for an online-learning during the operation of the biometric system 330, i.e. after deployment of the biometric system 330.

Using one or more training algorithms from the plurality of existing training algorithms to generate the Gaussian Mixture Model 815 has the advantage that simple and clear visualization of the overall system performance is achieved. Moreover, a current threshold value and even a matching score of ongoing matching performed by the underlying biometric system 330 are provided. When using the GMM that is trained as outlined above, it may be highlighted to a human supervisor what the decision of the GMM is going to be and why for an ongoing matching process. For example if the underlying biometric system 330 is a face recognition system, it could be shown that a current person is going to be rejected because the biometric sample was acquired under too dark conditions. Such information is very helpful for the human supervisor to intervene and mark the person as accepted. Further, a system administrator and/or supervisor may easily interpret the trained performance model. Moreover, some mixture modes 925 may be matched with different environmental conditions the underlying biometric system 330 is confronted with. For example, if the biometric system 330 is a facial recognition system where the biometric system 330 performs matches in order to automatically identify and/or verify a person from a digital image or a video frame of a video source and provides as output a correspondingly calculated matching score, some mixture modes 925 may be matched with different user demographics, such as gender, race or age. Optionally and/or alternatively, some mixture modes 925 may be matched with different environmental conditions and/or a combination of environmental and demographic measures. Optionally and/or alternatively, some mixture modes 925 may be matched with different impostor strategies. Matching the some of the mixture modes 925 with different environmental conditions has the advantage of providing an improved benchmarking, training and validation of the underlying biometric system 330. In particular, in order to be able to interpret the underlying model, it is necessary to understand which features, properties and/or patterns of the data the machine learning system was able to learn and how well. Although matching the some of the mixture modes 925 with different environmental conditions is not necessary for a proper functioning of the machine learning system as such, it has the advantage that it can be understood how good the quality is and how comprehensive the benchmarking and possible separate training data have been. Further, it can be validated that the system has indeed learned to adapt under the conditions that were required. Accordingly, it is necessary to link and/or visualize different categories, e.g. demographics, to the different mixture modes 925. Later on, when the mixture weight vector may be used as a part of the state-space vectors, this ability is even more advantageous since it allows describing the different states using the same categorization.

With regard to FIG. 9, the y-axis may represent a frequency 905, wherein the x-axis may represent a score 910. The dotted lines 915, 920 may represent the exemplary impostor 915 and genuine 920 distributions (cf. FIG. 7A). The solid lines, however, represent the individual mixture modes 925 related to the impostor distribution 915 and the genuine distribution 920, respectively. In particular, each normally distributed or mixture mode 925, N, hereinafter also called mixture component 925, is defined by
- its mean ($\mu_i$);
- its variance ($\sigma_i^2$); and/or
- its covariance ($\Sigma_i$) in a multidimensional case, e.g. a score fusion from multiple biometrics.

A mixture may then be defined as a weighted sum of the mixture components 925 using a weight factor (w) 930 containing a weight value ($w_i$) for each mixture component.

Unsupervised learning, supervised leaning and model selection may be used in pre-training, i.e. before deployment of the underlying biometric system 330, and online, i.e. after deployment of the underlying biometric system 330, to automatically learn an optimal number of mixture components 925, K, the parameters of each mixture component $\mu_i$, $\sigma_i^2$ and the weight values $w_i$. Model selection may be a technique for choosing among two or more models, e.g. among differently learned unsupervised models. In this phase, it can be visualized for each model which modelling error each model has, how well the model fits the data and/or how likely the model is, depending of the underlying algorithm. An exemplary choice with GMM might mainly be about a number of mixture modes 925, K, used. In a next step, the system might try to increase K. After a learning step, the system might see which model, i.e. having a number of mixture modes 925, K or K+1, fits the data best. The model having K+1 mixture modes 925 might only be selected if the model is significantly more accurate. This has the advantage that even a fully unsupervised learning system would not grow too complex.

Learning the performance model of the biometric system 330 as discussed above has the advantage that only score values of the underlying biometric system 330 are required as input. However, other data inputs and/or category labels of one or more of the samples may be provided as further performance input (810 as explained with reference to FIG. 8 above). For example, possible category labels may include a True Match (TM) and/or False Match (FM) and/or True Non-Match (TNM) and/or False Non-Match (FNM), wherein TM may be a number and/or rate of matches a biometric system 330 correctly decides as a match, FM may be a number/rate of matches 110 a biometric system 330 incorrectly decides as a match 110, TNM may be a number/rate of non-matches 130 a biometric system 330 correctly decides as a non-match 130 and FNM may be a number/rate of non-matches 110 a biometric system 330 incorrectly decides as a non-match 130. Optionally, confidence values may be assigned to each mixture mode 925. For example, mixture modes 925 learned from benchmarking and pre-training data may be assigned a high confidence value, wherein mixture modes 925 that are potentially added during operation of the underlying biometric system 330, e.g. to perform online fine-tuning of the biometric system 330, may be assigned a low confidence value.

Figure 10:
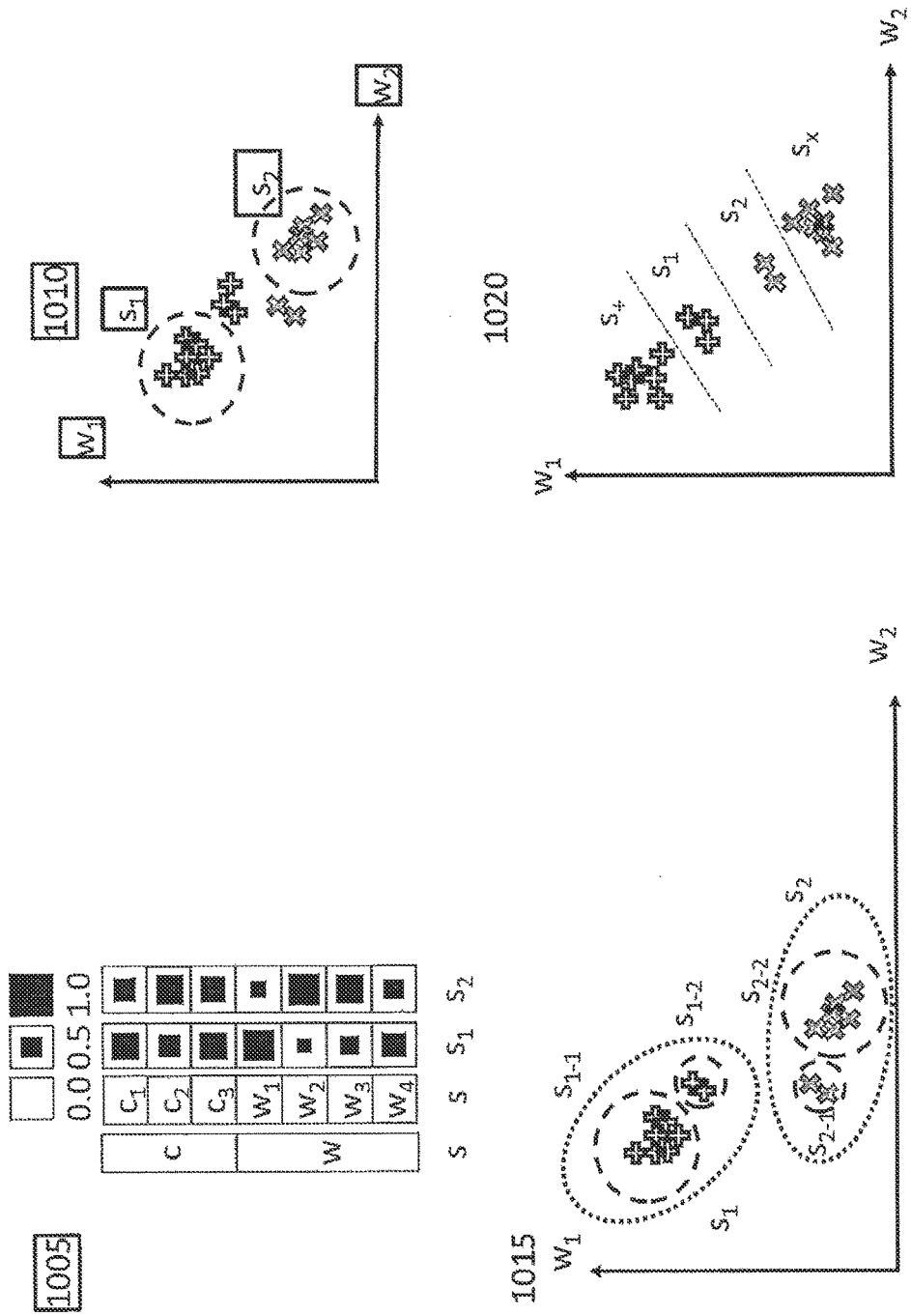
FIG. 10 shows an exemplary step of state-space clustering and classification.

FIG. 10 depicts the second step of generating a state-space clustering and classification model 830, as explained with reference to FIG. 8 above. This step takes as input the performance model weights 820, also referred to as weight factors (w) received from the GMM 815, as outlined with respect to FIG. 9 above. In particular, the weight factors 820 (w) from the GMM 815 may define a performance part of a state-space (c) of the underlying biometric system 330. Other parts of the state-space (c) may be defined by condition inputs 825 to the machine-learning system. Condition inputs 825 may e.g. comprise measures of environmental conditions and/or measures of device conditions, wherein device conditions may comprise device configuration variables, e.g. illumination or humidity of the underlying biometric system 330. Optionally, some or all of the condition inputs 825 may further be used as class labels in supervised learning. For example, condition inputs 825 that may affect the performance of the underlying biometric system 330 by definition, e.g. operational switches or modes, may be used as class labels in supervised learning.

Using the condition inputs 825 as class labels in supervised learning provides the technical advantage that the machine-learning system is able to learn faster, since only a reduced amount of data is needed. In particular, although an unsupervised learning system might be able to learn the same state-space form the performance observations alone, doing so requires a huge amount of data. Therefore, using the condition inputs requires less data since the underlying biometric system 330 is offered a suitable set of states the system functions under. Moreover, based on the performance model weights (w) 820 and the condition inputs 825, a state-space model 830 may be hierarchically constructed using suitable algorithms, e.g. Hierarchical Clustering, Support Vector Machine (SVM), Neural Networks (ANN) and/or Deep Learning. Constructing the state-space model 830 hierarchically has the advantage that the state of the underlying biometric system 330 may be defined in various levels of detail.

FIG. 10 depicts exemplary current states, also referred to as individual states 835, in the vector state-space. Vectors in a state space (s) may be clustered or classified into a plurality of vector groups. Clustering/classifying may be performed using distances from a centroid/mean state-space vector. Alternatively and/or additionally, clustering/classifying may be performed using a division hyper plane between the states.

Unsupervised learning, also referred to as unsupervised state space clustering 1010, may separate the most common states ($s_1$, $s_2$). Supervised learning, also referred to as supervised state-space clustering 1020, may find states that are relevant and provide an additional state description ($s_+$, $s_x$) that may occur in different conditions, even if they states may be rare. Additionally, transitions from one state to another state, e.g. when the underlying biometric system 330 traverses through the states, may be modeled. Transitions may be modeled by learning transition probabilities between each pair of states based on how frequently they appear in a training dataset (transition probability model). These probabilities may be used in order to validate state changes as they happen and/or in order to understand the typical conditions the system is operating under. Supervised learning 1020 has the technical advantage that the underlying biometric system 330 can learn that certain states represent impostor attacks or device malfunctions. Accordingly, the system might raise an alarm if such a state is reached.

Further, predictive modelling may be applied. Predictive models may be time-series models and/or predicting transition probability models. For example, when using a transition probability, a predictive model may guess the most likely net one or more states of the system and may already suggest a threshold value as output. The threshold value may be for example a calculated optimum threshold value for the current and for predicted states. The optimum threshold value may be calculated by building a weighted average of the optimum threshold for the current and the predicted states. Predictive modelling allows setting a threshold preemptively based on a predicted next state of the underlying biometric system 330.

In the case that mixture modes 925 are assigned with a confidence value as outlined with respect to FIG. 9 above, a similar aggregate value can be advantageously calculated for each state. For example, a similar aggregate value may be an aggregated confidence of a state. Since mixture mode 925 weights (w) may be part of the state-space vectors and since each mixture mode 925 might have a corresponding confidence value, the aggregated confidence of the state may be calculated as a weighted average of the corresponding confidence values. Such a value may be calculated using a confidence value of each mixture mode 925. Calculating the similar aggregate value has the technical advantage that the system may automatically disallow states having a very low confidence. Further, in a supervised learning approach, such states may be completely disallowed by using model selection in order to remove such models from the system. Additionally or alternatively, a human supervisor may be alerted when a state with very low confidence would be reached. Moreover, if during online fine-tuning of the underlying biometric system 330 mixture modes 925 are added or pruned, it is necessary to update the state-space model accordingly, e.g. by removing or adding elements to the state-space vectors.

Machine-Learning

FIGS. 11A to 13B depict how a machine-learning system as discussed with respect to FIGS. 2 to 4 and 8 to 10 above may be pre-trained. In particular, pre-training may be performed by learning from a benchmarking dataset and/or other pre-training datasets.

Figures 11A, 11B:
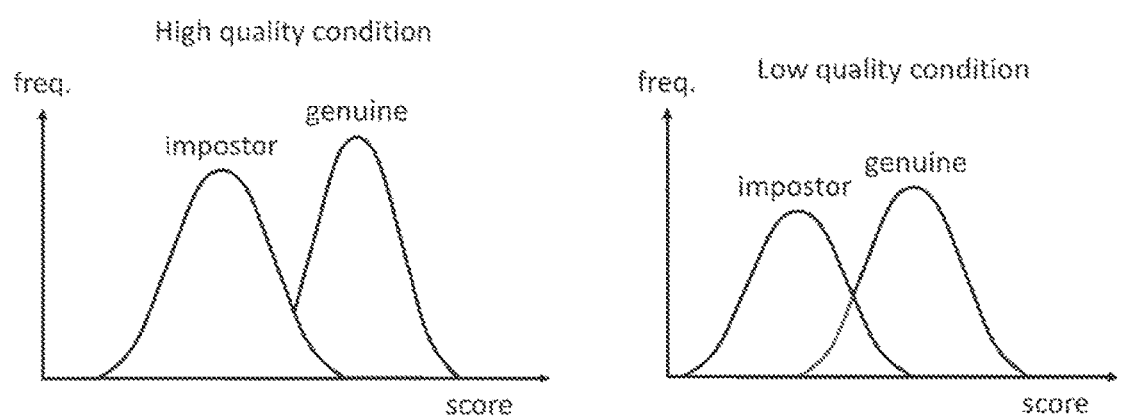
FIG. 11A shows an exemplary dataset containing samples of a high quality.
FIG. 11B shows an exemplary dataset containing samples of a low quality.

For Example, FIG. 11A illustrates an example of a dataset containing samples of a high quality. For example, if the biometric system 330 comprises a facial recognition system operable to automatically identify and/or verify a person from a digital image or a video frame of a video source, high quality samples may be acquired under bright lighting conditions. FIG. 11B illustrates an example of a dataset containing samples of a low quality, e.g. since they were acquired under bad lighting conditions.

Figures 12A, 12B:
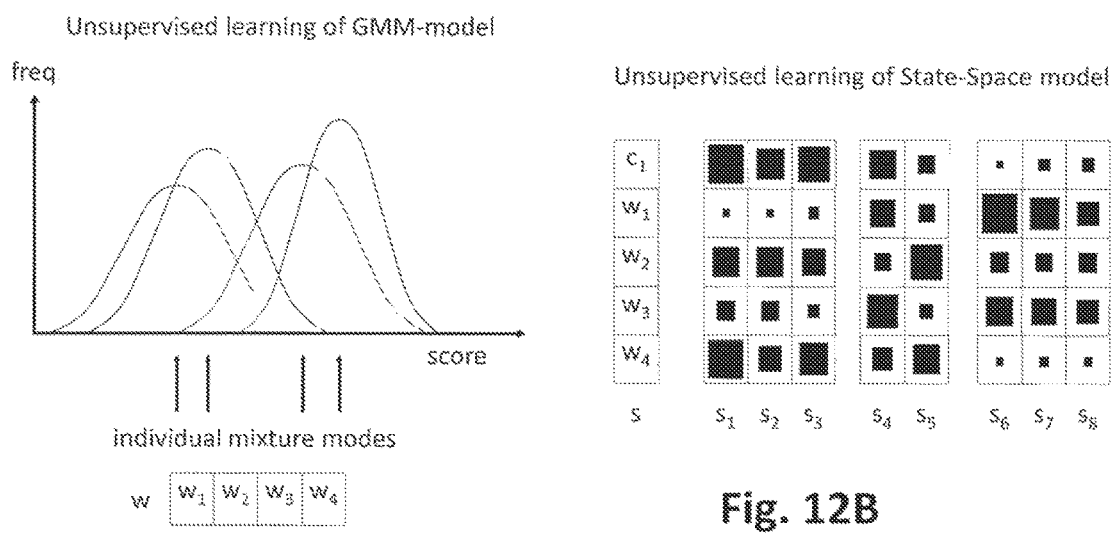
FIG. 12A depicts an exemplary GMM generated using unsupervised learning.
FIG. 12B shows an exemplary state-space model generated using unsupervised learning.

As shown in FIG. 12A, unsupervised learning of the GMM model leads towards building an accurate performance model. Further, as shown in FIG. 12B, unsupervised learning identifies a state-space that captures most common sample conditions.

As depicted in FIG. 13A, supervised learning enables fine-tuning of the models and provides a natural description of the models using the known labels. In particular, the mixture modes 925 and the individual states are classified in known categories. In this case, the known categories include genuine sample modes for low quality conditions ($W_{GL}$);
genuine sample modes for high quality conditions ($W_{GH}$);
high quality state under bright lighting conditions ($S_{BH}$);
mixed states under medium lighting ($S_{MH}$, $S_{ML}$);
conditional input variables (vector) for a sample quality ($C_Q$);
impostor sample modes for low quality conditions ($W_{IL}$);
impostor sample modes for high quality conditions ($W_{IH}$);
a state with dark lighting and low quality ($S_{DL}$).

Figure 14:
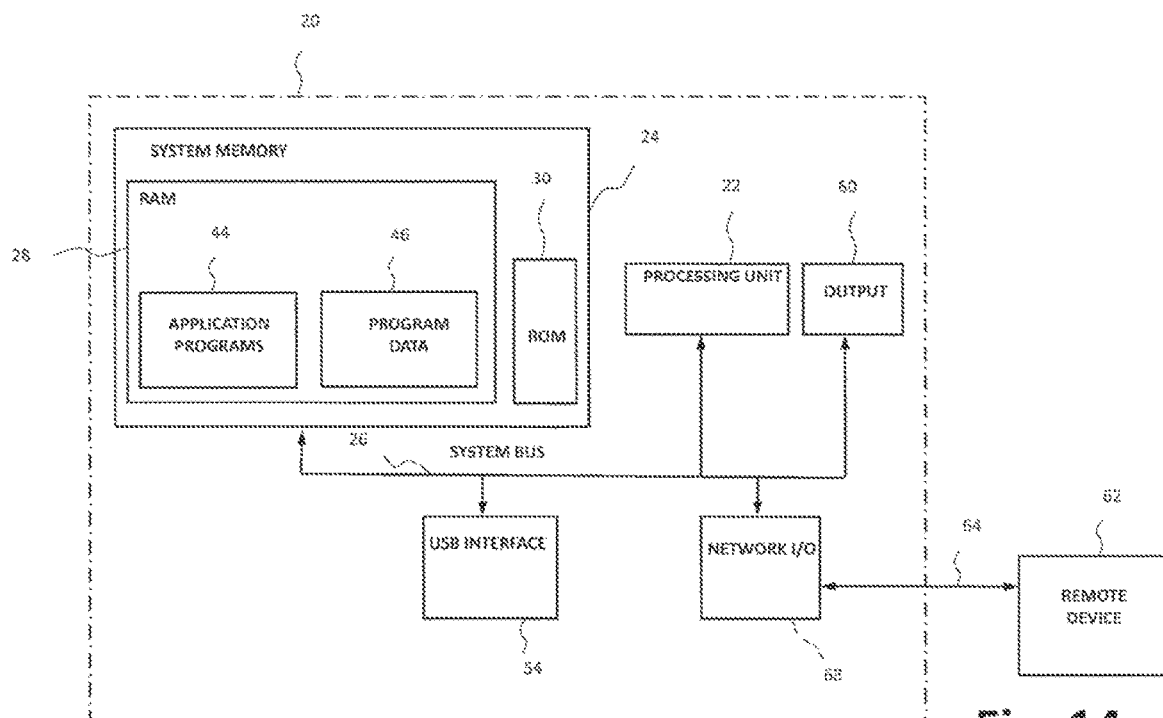
FIG. 14 depicts an exemplary computer environment.

FIG. 14 depicts a computer environment networked with a remote computer 62. The remote computer 62 may be another computing environment such as another mobile computer, a server, a router, a network PC, a peer device or other common network node, and may include many or all of the elements described above relative to the computing environment 20. The logical connections depicted in FIG. 5 include a local area network (LAN) 64. In addition, the mobile computer 20 may be connected to a wide area network (WAN) 66. Such networking environments are commonplace in offices, enterprise-wide computer networks, intranets and the Internet and may be encrypted.

When used in a LAN networking environment, the computing environment 20 may be connected to the LAN 64 through a network I/O 68. Furthermore, other data relevant to enabling an adaptively changing of a matching threshold in a biometric system may be resident on or accessible via the remote computer 62. It will be appreciated that the network connections shown are exemplary and other means of establishing a communications link between the electronic devices may be used.

The above-described computing system is only one example of the type of computing system that may be used to implement the computer-implemented method for adaptively changing a matching threshold in a biometric system using machine-learning.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set, and/or each embodiment described above in combination with every other embodiment in the specification.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A machine-learning system for adaptively changing a matching threshold in a biometric system to verify an identity of a subject, wherein the matching threshold is adapted to changing environmental conditions, the machine-learning system comprising:
a communication interface configured to communicatively couple the machine-learning system with the biometric system and an environmental sensor;
one or more memories; and
one or more processors, communicatively coupled to the one or more memories to:
receive, via the communication interface, input data from the biometric system,
the input data from the biometric system comprising biometric identification data samples received from a biometric sensor associated with the biometric system,
the biometric sensor being associated with at least one of:
a fingerprint reader,
a facial recognition system,
a retinal scanner, or
an iris scanner,
receive, via the communication interface, input data from the environmental sensor,
the input data from the environmental sensor comprising an environmental measure determined by the environmental sensor;
aggregate a batch of the received input data from the biometric system and from the environmental sensor;
compute a first suggestion for the matching threshold for the biometric system based on the aggregated batch and based on pre-determined identity information of the subject,
the first suggestion for the matching threshold being computed by using a first internal model, and
the first internal model comprising a first machine-learning algorithm executed by the machine-learning system;
compute a second suggestion for the matching threshold for the biometric system based on the aggregated batch and based on the pre-determined identity information of the subject,
the second suggestion being computed by using a second internal model,
the second internal model comprising a second machine-learning algorithm executed by the machine-learning system and different from the first machine-learning algorithm used by the first internal model;
compare the first suggestion for the matching threshold with the second suggestion for the matching threshold;
generate a final suggestion for the matching threshold based on the comparison;
output, via the communication interface, the final suggestion for the matching threshold to the biometric system;
receive a matching score, associated with the identity of the subject, from the biometric system based on the final suggestion for the matching threshold and the pre-determined identity information of the subject;
authenticate the subject when the matching score indicates an identity match; and
refuse to authenticate the subject when the matching score indicates no identity match.

2. The machine-learning system of claim 1, wherein the input data includes one or more of:
biometric data quality measures, wherein the biometric data quality measures relate to a quality of biometric data samples;
biometric system performance measures including a False Acceptance Rate (FAR) and a False Rejection Rate (FRR);
state indicators comprising a throughput and a time of day;
allowed limits of the biometric system comprising a minimum matching threshold value and a maximum FAR; or
benchmark testing results,
wherein the benchmark testing results are retrieved from a benchmark test performed on the biometric system before deployment.

3. The machine-learning system of claim 1, wherein, when aggregating the batch of the received input data, the one or more processors are to:
collect statistics on matches performed by the biometric system;
wherein, when collecting the statistics, the one or more processors are to:
collect input data and output values of the matches performed by the biometric system during a batch window; and
label the matches as true/false matches or true/false non-matches based on a ground truth.

4. The machine-learning system of claim 1, where the one or more processors are further to:
normalize the input data in the aggregated batch, and
compute additional parameters from the normalized input data within the aggregated batch,
wherein, when computing of the additional parameters, the one or more processors are to at least one of:
compute a mean of the normalized input data,
compute a variance of the normalized input data; or
compute a histogram of the normalized input data.

5. The machine-learning system of claim 1, wherein the machine-learning system is operable to:
store the aggregated batch in a storage device; and
wherein the aggregated batch is re-sampled for continuous learning.

6. The machine-learning system of claim 1, wherein the first internal model is updated based on the aggregated batch using the first machine-learning algorithm; and wherein the second internal model is updated based on the aggregated batch using the second machine-learning algorithm different from the first machine-learning algorithm.

7. A computer-implemented method for adaptively changing a matching threshold in a biometric system to verify an identity of a subject using machine-learning, wherein the matching threshold is adapted to changing environmental conditions, the method comprising:
receiving, by a network device, input data from the biometric system via a communication interface,
the communication interface being configured to communicatively couple the network device with the biometric system and an environmental sensor;
the input data from the biometric system comprising biometric identification data samples received from a biometric sensor associated with the biometric system,
the biometric sensor being associated with at least one of:
a fingerprint reader,
a facial recognition system,
a retinal scanner, or
an iris scanner,
receiving, by the network device and via the communication interface, input data from the environmental sensor,
the input data from the environmental sensor comprising an environmental measure determined by the environmental sensor;
aggregating, by the network device, a batch of the received input data from the biometric system and the environmental sensor;
computing, by the network device, a first suggestion for the matching threshold of the biometric system based on the aggregated batch and based on pre-determined identity information of the subject,
the first suggestion for the matching threshold being computed by using a first internal model, and
the first internal model comprising a first machine-learning algorithm executed by the network device;
computing, by the network device, a second suggestion for the matching threshold of the biometric system based on the aggregated batch and based on the pre-determined identity information of the subject,
second suggestions being computed by using a second internal model,
the second internal model comprising a second machine-learning algorithm executed by the network device and different from the first machine-learning algorithm used by the first internal model;
comparing, by the network device, the first suggestion for the matching threshold with the second suggestion for the matching threshold to generate a final suggestion for the matching threshold of the biometric system based on the comparison;
outputting, by the network device, the final suggestion for the matching threshold of the biometric system via the communication interface;
receiving, by the network device, a matching score, associated with the identity of the subject, from the biometric system based on the final suggestion for the matching threshold and the pre-determined identity information of the subject;
authenticating, by the network device, the subject when the matching score indicates an identity match; and
refusing, by the network device, to authenticate the subject when the matching score indicates no identity match.

8. The method of claim 7, wherein the input data includes one or more of:
biometric data quality measures, wherein the biometric data quality measures relate to a quality of biometric data samples;
biometric system performance measures including a False Acceptance Rate (FAR), and a False Rejection Rate (FRR);
state indicators comprising a throughput and a time of day;
allowed limits of the biometric system comprising a minimum matching threshold value and a maximum FAR; or
benchmark testing results,
wherein the benchmark testing results are retrieved from a benchmark test performed on the biometric system before deployment.

9. The method of claim 7, wherein aggregating the batch of the received input data comprises:
collecting statistics on matches performed by the biometric system;
wherein collecting the statistics comprises:
collecting input data and output values of the matches performed by the biometric system during a batch window; and
labelling the matches as true/false matches or true/false non-matches based on a ground truth.

10. The method of claim 7, further comprising:
normalizing the input data in the aggregated batch; and
computing additional parameters from the normalized input data in the aggregated batch; and
wherein computing the additional parameters from the normalized input data within the aggregated batch comprises one or more of:
computing a mean of the normalized input data,
computing a variance of the normalized input data, or
computing a histogram of the normalized input data.

11. The method of claim 7, further comprising:
storing the aggregated batch in a storage device,
wherein the aggregated batch is re-sampled for continuous learning.

12. The method of claim 7, further comprising:
updating the first internal model based on the aggregated batch using the first machine-learning algorithm; and
updating the second internal model based on the aggregated batch using the second machine-learning algorithm different from the first machine-learning algorithm.

13. The method of claim 7, wherein the environmental measure includes at least one of:
lighting conditions,
humidity, or
data related to demographics of users using the biometric system.

14. A non-transitory computer-readable medium storing instructions, the instructions comprising:
one or more instructions that, when executed by a network device, cause the network device to:
receive input data from a biometric system via a communication interface,
the communication interface configured to communicatively couple the machine-learning system with the biometric system and an environmental sensor, wherein the biometric system is to verify an identity of a subject,
wherein the input data from the biometric system comprises biometric identification data samples received from a biometric sensor associated with the biometric system,
wherein the biometric sensor is associated with at least one of:
a fingerprint reader,
a facial recognition system,
a retinal scanner, or
an iris scanner,
receive, via the communication interface, input data from the environmental sensor,
the input data from the environmental sensor comprising an environmental measure determined by the environmental sensor;
aggregate a batch of the received input data from the biometric system and from the environmental sensor;
compute a first suggestion for a matching threshold of the biometric system based on the aggregated batch and based on pre-determined identity information of the subject,
wherein computing the first suggestion for the matching threshold is performed using a first internal model, and
wherein the first internal model comprises a first machine-learning algorithm executed by the network device;
compute a second suggestion for the matching threshold of the biometric system based on the aggregated batch and based on the pre-determined identity information of the subject,
wherein computing the second suggestion uses a second internal model,
wherein the second internal model comprises a second machine-learning algorithm executed by the network device and different from the first machine-learning algorithm used by the first internal model;
compare the first suggestion for the matching threshold with the second suggestion for the matching threshold to generate a final suggestion for the matching threshold of the biometric system based on the comparison;
output the final suggestion for the matching threshold of the biometric system via the communication interface;
receive a matching score, associated with the identity of the subject, from the biometric system based on the final suggestion for the matching threshold and the pre-determined identity information of the subject;
authenticate the subject when the matching score indicates an identity match; and
refuse to authenticate the subject when the matching score indicates no identity match.

15. The non-transitory computer-readable medium of claim 14, wherein the input data includes one or more of:
biometric data quality measures, wherein the biometric data quality measures relate to a quality of biometric data samples;
biometric system performance measures including a False Acceptance Rate (FAR), and a False Rejection Rate (FRR);
state indicators comprising a throughput and a time of day;
allowed limits of the biometric system comprising a minimum matching threshold value and a maximum FAR; or
benchmark testing results,
wherein the benchmark testing results are retrieved from a benchmark test performed on the biometric system before deployment.

16. The non-transitory computer-readable medium of claim 14, wherein the one or more instructions that cause the network device to aggregate the batch of the received input data cause the network device to:
collect statistics on matches performed by the biometric system;
wherein the one or more instructions that cause the network device to collect the statistics on the matches cause the network device to:
collect input data and output values of the matches performed by the biometric system during a batch window; and
label the matches as true/false matches or true/false non-matches based on aground truth.

17. The non-transitory computer-readable medium of claim 14, wherein the instructions further comprise:
one or more instructions that cause the network device to normalize the input data in the aggregated batch; and
one or more instructions that cause the network device to compute additional parameters from the normalized input data in the aggregated batch; and
wherein the one or more instructions to cause the network device to compute the additional parameters from the normalized input data within the aggregated batch cause the network device to one or more of:
compute a mean of the normalized input data,
compute a variance of the normalized input data, or
compute a histogram of the normalized input data.

18. The non-transitory computer-readable medium of claim 14, wherein the instructions further comprise:
one or more instructions that cause the network device to store the aggregated batch in a storage device,
wherein the aggregated batch is re-sampled for continuous learning.

19. The non-transitory computer-readable medium of claim 14, wherein the instructions further comprise:
one or more instructions that cause the network device to update the first internal model based on the aggregated batch using the first machine-learning algorithm; and
one or more instructions that cause the network device to update the second internal model based on the aggregated batch using the second machine-learning algorithm different from the first machine-learning algorithm.

20. The non-transitory computer-readable medium of claim 14, wherein the environmental measure includes at least one of:
lighting conditions,
humidity, or
data related to demographics of users using the biometric system.

* * * * *